(12) United States Patent
Tonomura et al.

(10) Patent No.: US 9,024,051 B2
(45) Date of Patent: May 5, 2015

(54) ORGANOXYSILANE COMPOUNDS HAVING SILYL-PROTECTED SECONDARY AMINO GROUP AND MAKING METHOD

(71) Applicant: Shin-Etsu Chemical Co., Ltd., Tokyo (JP)

(72) Inventors: Yoichi Tonomura, Joetsu (JP); Tohru Kubota, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 256 days.

(21) Appl. No.: 13/872,407

(22) Filed: Apr. 29, 2013

(65) Prior Publication Data

US 2013/0296593 A1 Nov. 7, 2013

(30) Foreign Application Priority Data

May 1, 2012 (JP) ................................ 2012-104369

(51) Int. Cl.
*C07F 7/18* (2006.01)

(52) U.S. Cl.
CPC ............. *C07F 7/1808* (2013.01); *C07F 7/1836* (2013.01); *C07F 7/184* (2013.01)

(58) Field of Classification Search
CPC ....................................................... C07F 7/1808
USPC ............................................................ 556/410
See application file for complete search history.

(56) References Cited

FOREIGN PATENT DOCUMENTS

| JP | 2002-193976 A | | 7/2002 |
|---|---|---|---|
| JP | 2006-16370 A | | 1/2006 |
| JP | 2006-16580 A | | 1/2006 |
| JP | 2006016580 A | * | 1/2006 |
| JP | 2007-55950 A | | 3/2007 |
| JP | 2011-162496 A | | 8/2011 |

OTHER PUBLICATIONS

European Search Report, dated Aug. 20, 2013, for European Application No. 13165895.7.
Nomura et al., "Synthesis of Novel Moisture-Curable Polyurethanes End-Capped with Trialkoxysilane and Their Application to One-Component Adhesives", Journal of Polymer Science, Part A: Polymer Chemistry 45, pp. 2689-2704, 2007.

* cited by examiner

*Primary Examiner* — Porfirio Nazario Gonzalez
*Assistant Examiner* — Kofi Adzamli
(74) *Attorney, Agent, or Firm* — Birch, Stewart, Kolasch & Birch, LLP

(57) ABSTRACT

A silane compound having a secondary amino group protected with a specific silyl group is useful as silane coupling agent, resin additive, textile treating agent, surface treating agent, paint additive, and adhesive.

4 Claims, 12 Drawing Sheets

ORGANOXYSILANE COMPOUNDS HAVING SILYL-PROTECTED SECONDARY AMINO GROUP AND MAKING METHOD

CROSS-REFERENCE TO RELATED APPLICATION

This non-provisional application claims priority under 35 U.S.C. §119(a) on Patent Application No. 2012-1014369 filed in Japan on May 1, 2012, the entire contents of which are hereby incorporated by reference.

TECHNICAL FIELD

This invention relates to novel organoxysilane compounds having a silyl-protected secondary amino group and a method of preparing the same. These compounds are useful as silane coupling agent, resin additive, textile treating agent, surface treating agent, paint additive, adhesive and the like.

BACKGROUND ART

Organoxysilane compounds having an amino group are useful as resin additive, paint additive, adhesive, silane coupling agent, textile treating agent, and surface treating agent. Known organoxysilane compounds include organoxysilane compounds having a primary amino group such as aminopropyltrimethoxysilane, organoxysilane compounds having a secondary amino group such as N-phenylaminopropyltrimethoxysilane, and organoxysilane compounds having a tertiary amino group such as dimethylaminopropyltrimethoxysilane.

Of these organoxysilane compounds having an amino group, organoxysilane compounds having a secondary amino group such as N-phenylaminopropyltrimethoxysilane and N-ethylaminoisobutyltrimethoxysilane are useful as a polyurethane modifying agent. Advantageously, they cause a reduced viscosity buildup after modification as compared with the organoxysilane compounds having a primary amino group, as reported in Non-Patent Document 1.

CITATION LIST

Non-Patent Document 1: Journal of Polymer Science, Part A: Polymer Chemistry (2007), 45 (13), 2689-2704

DISCLOSURE OF INVENTION

A problem arises when the organoxysilane compound having a secondary amino group is used as a modifying agent for polyurethane. The modified polyurethane shows a viscosity buildup as compared with the viscosity immediately after addition although the viscosity buildup after modification is small as compared with the use of the organoxysilane compound having a primary amino group. Such a viscosity buildup occurs because the secondary amino group has a hydrogen atom bonded to the nitrogen atom. That is, when a silane compound having a secondary amino group is in admixture with a polyurethane precursor, the amino group can react with an isocyanate group in the polyurethane precursor. Particularly when the silane compound is added to a composition containing many isocyanate, epoxy and/or acid anhydride groups, the reaction can proceed until the composition is cured. Thus the composition cannot be a one-part system, but a two-part system wherein the silane compound is added and mixed immediately before use. The two-part composition is cumbersome to handle because two parts must be accurately weighed and mixed.

The above problem may be solved by protecting the organoxysilane compound having a secondary amino group with a trimethylsilyl group which is commonly used as the protective group. Since the bond between nitrogen and trimethylsilyl is less stable, a one-part composition, if components are formulated so, undergoes a viscosity buildup and even cures as a result of cleavage of the nitrogen-trimethylsilyl bond with the lapse of time.

An object of the invention is to provide an amino-containing silane compound which has no hydrogen atom on the nitrogen atom, prevents the functional group itself from reaction stably when added to resin, paint or adhesive, and on use, generates active hydrogen to resume the functional group in a quantitative and efficient manner; and a method of preparing the same.

The inventors have found that a silane compound having a secondary amino group protected with a specific silyl group to prevents the functional group itself from reaction stably when added to resin, paint or adhesive, and on use, generates active hydrogen by capturing moisture in air, so that it may exert an addition effect equivalent to an organosilicon compound having a secondary amino group.

In one aspect, the invention provides an organoxysilane compound having a silyl-protected secondary amino group, represented by the general formula (1):

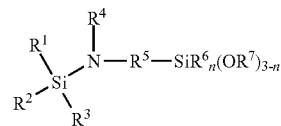

(1)

wherein i) $R^1$ is a substituted or unsubstituted, secondary or tertiary, monovalent hydrocarbon group of 3 to 20 carbon atoms, and $R^2$, $R^3$, $R^4$, $R^6$ and $R^7$ each are a substituted or unsubstituted, monovalent hydrocarbon group of 1 to 20 carbon atoms, or ii) $R^1$, $R^2$ and $R^3$ each are a substituted or unsubstituted, monovalent hydrocarbon group of 2 to 20 carbon atoms, and $R^4$, $R^6$ and $R^7$ each are a substituted or unsubstituted, monovalent hydrocarbon group of 1 to 20 carbon atoms, and in either case, $R^5$ is a straight or branched divalent hydrocarbon group of 1 to 20 carbon atoms, and n is 0 or 1.

Typically, the $R^1R^2R^3Si$— group is t-butyldimethylsilyl or triisopropylsilyl.

In another aspect, the invention provides a method of preparing the organoxysilane compound defined above, comprising the step of reacting a compound having the general formula (2):

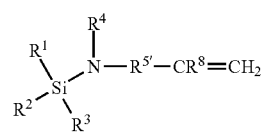

(2)

wherein $R^1$, $R^2$, $R^3$, and $R^4$ are as defined above, $R^8$ is hydrogen or methyl, $R^{5'}$ is a straight or branched divalent hydrocarbon group of 1 to 18 carbon atoms when $R^8$ is hydrogen, or $R^{5'}$ is a straight or branched divalent hydrocarbon group of 1 to 17 carbon atoms when $R^8$ is methyl, with a hydrogensilane compound having the general formula (3):

$$HSiR^6{}_n(OR^7)_{3-n} \qquad (3)$$

wherein $R^6$, $R^7$ and n are as defined above, in the presence of a platinum catalyst.

In a further aspect, the invention provides a method of preparing the organoxysilane compound defined above, comprising the step of silylating a compound having the general formula (4):

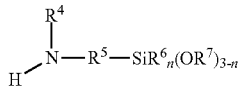
(4)

wherein $R^4$, $R^5$, $R^6$, $R^7$ and n are as defined above, with a silylating agent having a $R^1R^2R^3Si$— group wherein $R^1$, $R^2$ and $R^3$ are as defined above.

ADVANTAGEOUS EFFECT OF INVENTION

The organoxysilane compound having a silyl-protected secondary amino group prevents its own functional group from reaction stably when used as resin additive, paint additive, adhesive, silane coupling agent, textile treating agent, and surface treating agent, and on use, generates active hydrogen by capturing moisture in air, with an improvement in properties being achieved by its addition. The compound is useful as resin additive, paint additive, adhesive, silane coupling agent, textile treating agent, and surface treating agent.

DESCRIPTION OF PREFERRED EMBODIMENTS

Figure 1:
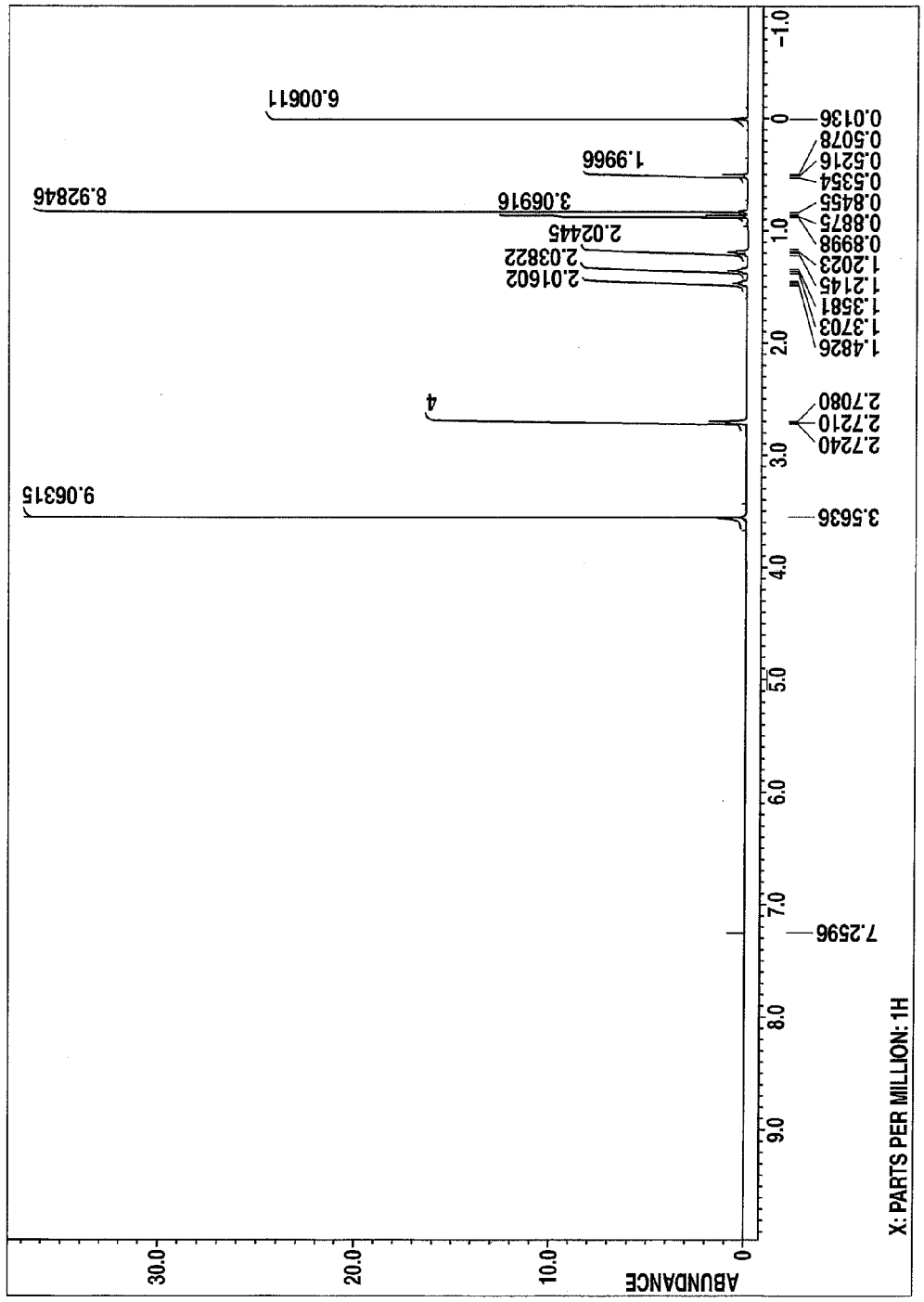
FIGS. 1 and 2 diagrammatically illustrate the $^1$H-NMR and IR spectra of N-t-butyldimethylsilyl-N-butyl-3-aminopropyl-trimethoxysilane obtained in Example 1, respectively.

The notation (Cn-Cm) means a group containing from n to m carbon atoms per group.

One embodiment of the invention is an organoxysilane compound having a secondary amino group protected with a silyl group. The compound has the general formula (1).

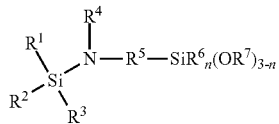
(1)

Herein i) $R^1$ is a substituted or unsubstituted, secondary or tertiary, monovalent hydrocarbon group of 3 to 20 carbon atoms, and $R^2$, $R^3$, $R^4$, $R^6$ and $R^7$ each are a substituted or unsubstituted, monovalent hydrocarbon group of 1 to 20 carbon atoms, or ii) $R^1$, $R^2$ and $R^3$ each are a substituted or unsubstituted, monovalent hydrocarbon group of 2 to 20 carbon atoms, and $R^4$, $R^6$ and $R^7$ each are a substituted or unsubstituted, monovalent hydrocarbon group of 1 to 20 carbon atoms. In either case i) or ii), $R^5$ is a straight or branched divalent hydrocarbon group of 1 to 20 carbon atoms, and n is 0 or 1.

In case i), $R^1$ is a substituted or unsubstituted, secondary or tertiary, monovalent hydrocarbon group of 3 to 20 carbon atoms, and $R^2$, $R^3$, $R^4$, $R^6$ and $R^7$ each are a substituted or unsubstituted, monovalent hydrocarbon group of 1 to 20 carbon atoms. Examples of group $R^1$ include secondary alkyl groups such as isopropyl, sec-butyl, cyclopentyl, cyclohexyl, aryl groups such as phenyl and tolyl, and tertiary alkyl groups such as t-butyl, thexyl, and methylcyclohexyl, with isopropyl and t-butyl being preferred. Some or all hydrogen atoms on these hydrocarbon groups may be substituted. Suitable substituent groups include alkoxy groups such as methoxy, ethoxy, and (iso)propoxy, halogen atoms such as fluorine, chlorine, bromine and iodine, cyano groups, amino groups, phenyl groups, $C_6$-$C_{18}$ aryl groups such as tolyl, $C_7$-$C_{18}$ aralkyl groups such as benzyl and phenethyl, $C_2$-$C_{10}$ acyl groups, trialkylsilyl, trialkoxysilyl, dialkylmonoalkoxysilyl or monoalkyldialkoxysilyl groups each having a $C_1$-$C_5$ alkyl and/or $C_1$-$C_5$ alkoxy moiety. The foregoing groups may be separated by an ester (—COO—), ether (—O—), sulfide (—S—) or similar radical. A combination of two or more of the foregoing is also included.

$R^2$, $R^3$, $R^4$, $R^6$ and $R^7$ each are a substituted or unsubstituted, monovalent hydrocarbon group of 1 to 20 carbon atoms, examples of which include straight, branched or cyclic alkyl, alkenyl, aryl and aralkyl groups. Suitable groups include straight alkyl groups such as methyl, ethyl, propyl, butyl, pentyl, hexyl, heptyl, octyl, decyl, dodecyl, tetradecyl, hexadecyl, octadecyl, and eicosyl; branched alkyl groups such as isopropyl, isobutyl, sec-butyl, tert-butyl, thexyl, and 2-ethylhexyl; cyclic alkyl groups such as cyclopentyl and cyclohexyl; alkenyl groups such as vinyl, allyl and propenyl; aryl groups such as phenyl and tolyl; and aralkyl groups such as benzyl. Inter alia, methyl, ethyl, isopropyl, sec-butyl, and tert-butyl are preferred. Some or all hydrogen atoms on these hydrocarbon groups may be substituted. Suitable substituent groups are as exemplified for $R^1$.

In case ii), $R^1$, $R^2$ and $R^3$ each are a substituted or unsubstituted, monovalent hydrocarbon group of 2 to 20 carbon atoms, and $R^4$, $R^6$ and $R^7$ each are a substituted or unsubstituted, monovalent hydrocarbon group of 1 to 20 carbon atoms. Suitable hydrocarbon groups represented by $R^1$, $R^2$ and $R^3$ are those groups exemplified above for $R^2$, $R^3$, $R^4$, $R^6$ and $R^7$ in case i), except methyl. Suitable hydrocarbon groups represented by $R^4$, $R^6$ and $R^7$ are those groups exemplified above for $R^2$, $R^3$, $R^4$, $R^6$ and $R^7$ in case i).

Of cases i) and ii), case i) is preferred, that is, a combination of $R^1$ which is a substituted or unsubstituted, secondary or tertiary, monovalent hydrocarbon group of 3 to 20 carbon atoms, with $R^2$, $R^3$, $R^4$, $R^6$ and $R^7$ which each are a substituted or unsubstituted, monovalent hydrocarbon group of 1 to 20 carbon atoms is preferred. Also preferably, the $R^1R^2R^3Si$— group is t-butyldimethylsilyl or triisopropylsilyl.

$R^5$ is a straight or branched divalent hydrocarbon group of 1 to 20 carbon atoms, examples of which include alkylene groups such as methylene, dimethylene, trimethylene, tetramethylene, hexamethylene, octamethylene, decamethylene, and isobutylene, arylene groups such as phenylene, and aralkylene groups such as methylenephenylene and methylenephenylenemethylene.

Examples of the organoxysilane compound having a silyl-protected secondary amino group, represented by formula (1) include N-triethylsilyl-N-methylaminomethyltrimethoxysilane, N-triethylsilyl-N-methylaminomethylmethyldimethoxysilane, N-triethylsilyl-N-methylaminomethyltriethoxysilane, N-triethylsilyl-N-methylaminomethylmethyldiethoxysilane, N-triethylsilyl-N-methyl-2-aminoethyltrimethoxysilane, N-triethylsilyl-N-methyl-2-aminoethylmethyldimethoxysilane, N-triethylsilyl-N-methyl-2-aminoethyltriethoxysilane, N-triethylsilyl-N-methyl-2-aminoethylmethyldiethoxysilane, N-triethylsilyl-N-methyl-3-aminopropyltrimethoxysilane, N-triethylsilyl-N-methyl-3-aminopropylmethyldimethoxysilane, N-triethylsilyl-N-methyl-3-aminopropyltriethoxysilane, N-triethylsilyl-N-methyl-3-aminopropylmethyldiethoxysilane, N-triethylsilyl-N-methyl-4-aminobutyltrimethoxysilane, N-triethylsilyl-N-methyl-4-aminobutylmethyldimethoxysilane, N-triethylsilyl-N-methyl-4-aminobutyltriethoxysilane, N-triethylsilyl-N-methyl-4-aminobutylmethyldiethoxysilane, N-triethylsilyl-N-ethylaminomethyltrimethoxysilane, N-triethylsilyl-N-ethylaminomethylmethyldimethoxysilane, N-triethylsilyl-N-ethylaminomethyltriethoxysilane, N-triethylsilyl-N-ethylaminomethylmethyldiethoxysilane, N-triethylsilyl-N-ethyl-2-aminoethyltrimethoxysilane, N-triethylsilyl-N-ethyl-2-aminoethylmethyldimethoxysilane, N-triethylsilyl-N-ethyl-2-aminoethyltriethoxysilane, N-triethylsilyl-N-ethyl-2-aminoethylmethyldiethoxysilane, N-triethylsilyl-N-ethyl-3-aminopropyltrimethoxysilane, N-triethylsilyl-N-ethyl-3-aminopropylmethyldimethoxysilane, N-triethylsilyl-N-ethyl-3-aminopropyltriethoxysilane, N-triethylsilyl-N-ethyl-3-aminopropylmethyldiethoxysilane, N-triethylsilyl-N-ethyl-4-aminobutyltrimethoxysilane, N-triethylsilyl-N-ethyl-4-aminobutylmethyldimethoxysilane, N-triethylsilyl-N-ethyl-4-aminobutyltriethoxysilane, N-triethylsilyl-N-ethyl-4-aminobutylmethyldiethoxysilane, N-triethylsilyl-N-butylaminomethyltrimethoxysilane, N-triethylsilyl-N-butylaminomethylmethyldimethoxysilane, N-triethylsilyl-N-butylaminomethyltriethoxysilane, N-triethylsilyl-N-butylaminomethylmethyldiethoxysilane, N-triethylsilyl-N-butyl-2-aminoethyltrimethoxysilane, N-triethylsilyl-N-butyl-2-aminoethylmethyldimethoxysilane, N-triethylsilyl-N-butyl-2-aminoethyltriethoxysilane, N-triethylsilyl-N-butyl-2-aminoethylmethyldiethoxysilane, N-triethylsilyl-N-butyl-3-aminopropyltrimethoxysilane, N-triethylsilyl-N-butyl-3-aminopropylmethyldimethoxysilane, N-triethylsilyl-N-butyl-3-aminopropyltriethoxysilane, N-triethylsilyl-N-butyl-3-aminopropylmethyldiethoxysilane, N-triethylsilyl-N-butyl-4-aminobutyltrimethoxysilane, N-triethylsilyl-N-butyl-4-aminobutylmethyldimethoxysilane, N-triethylsilyl-N-butyl-4-aminobutyltriethoxysilane, N-triethylsilyl-N-butyl-4-aminobutylmethyldiethoxysilane, N-triethylsilyl-N-cyclohexylaminomethyltrimethoxysilane, N-triethylsilyl-N-cyclohexylaminomethylmethyldimethoxysilane, N-triethylsilyl-N-cyclohexylaminomethyltriethoxysilane, N-triethylsilyl-N-cyclohexylaminomethylmethyldiethoxysilane, N-triethylsilyl-N-cyclohexyl-2-aminoethyltrimethoxysilane, N-triethylsilyl-N-cyclohexyl-2-aminoethylmethyldimethoxysilane, N-triethylsilyl-N-cyclohexyl-2-aminoethyltriethoxysilane, N-triethylsilyl-N-cyclohexyl-2-aminoethylmethyldiethoxysilane, N-triethylsilyl-N-cyclohexyl-3-aminopropyltrimethoxysilane, N-triethylsilyl-N-cyclohexyl-3-aminopropylmethyldimethoxysilane, N-triethylsilyl-N-cyclohexyl-3-aminopropyltriethoxysilane, N-triethylsilyl-N-cyclohexyl-3-aminopropylmethyldiethoxysilane, N-triethylsilyl-N-cyclohexyl-4-aminobutyltrimethoxysilane, N-triethylsilyl-N-cyclohexyl-4-aminobutylmethyldimethoxysilane, N-triethylsilyl-N-cyclohexyl-4-aminobutyltriethoxysilane, N-triethylsilyl-N-cyclohexyl-4-aminobutylmethyldiethoxysilane, N-triethylsilyl-N-phenylaminomethyltrimethoxysilane, N-triethylsilyl-N-phenylaminomethylmethyldimethoxysilane, N-triethylsilyl-N-phenylaminomethyltriethoxysilane, N-triethylsilyl-N-phenylaminomethylmethyldiethoxysilane, N-triethylsilyl-N-phenyl-2-aminoethyltrimethoxysilane, N-triethylsilyl-N-phenyl-2-aminoethylmethyldimethoxysilane, N-triethylsilyl-N-phenyl-2-aminoethyltriethoxysilane, N-triethylsilyl-N-phenyl-2-aminoethylmethyldiethoxysilane, N-triethylsilyl-N-phenyl-3-aminopropyltrimethoxysilane, N-triethylsilyl-N-phenyl-3-aminopropylmethyldimethoxysilane, N-triethylsilyl-N-phenyl-3-aminopropyltriethoxysilane, N-triethylsilyl-N-phenyl-3-aminopropylmethyldiethoxysilane, N-triethylsilyl-N-phenyl-4-aminobutyltrimethoxysilane, N-triethylsilyl-N-phenyl-4-aminobutylmethyldimethoxysilane, N-triethylsilyl-N-phenyl-4-aminobutyltriethoxysilane, N-triethylsilyl-N-phenyl-4-aminobutylmethyldiethoxysilane, N-triethylsilyl-N-benzylaminomethyltrimethoxysilane, N-triethylsilyl-N-benzylaminomethylmethyldimethoxysilane, N-triethylsilyl-N-benzylaminomethyltriethoxysilane, N-triethylsilyl-N-benzylaminomethylmethyldiethoxysilane, N-triethylsilyl-N-benzyl-2-aminoethyltrimethoxysilane, N-triethylsilyl-N-benzyl-2-aminoethylmethyldimethoxysilane, N-triethylsilyl-N-benzyl-2-aminoethyltriethoxysilane, N-triethylsilyl-N-benzyl-2-aminoethylmethyldiethoxysilane, N-triethylsilyl-N-benzyl-3-aminopropyltrimethoxysilane, N-triethylsilyl-N-benzyl-3-aminopropylmethyldimethoxysilane, N-triethylsilyl-N-benzyl-3-aminopropyltriethoxysilane, N-triethylsilyl-N-benzyl-3-aminopropylmethyldiethoxysilane, N-triethylsilyl-N-benzyl-4-aminobutyltrimethoxysilane, N-triethylsilyl-N-benzyl-4-aminobutylmethyldimethoxysilane, N-triethylsilyl-N-benzyl-4-aminobutyltriethoxysilane, N-triethylsilyl-N-benzyl-4-aminobutylmethyldiethoxysilane, N-t-butyldimethylsilyl-N-methylaminomethyltrimethoxysilane, N-t-butyldimethylsilyl-N-methylaminomethylmethyldimethoxysilane, N-t-butyldimethylsilyl-N-methylaminomethyltriethoxysilane, N-t-butyldimethylsilyl-N-methylaminomethylmethyldiethoxysilane, N-t-butyldimethylsilyl-N-methyl-2-aminoethyltrimethoxysilane, N-t-butyldimethylsilyl-N-methyl-2-aminoethylmethyldimethoxysilane, N-t-butyldimethylsilyl-N-methyl-2-aminoethyltriethoxysilane, N-t-butyldimethylsilyl-N-methyl-2-aminoethylmethyldiethoxysilane, N-t-butyldimethylsilyl-N-methyl-3-aminopropyltrimethoxysilane, N-t-butyldimethylsilyl-N-methyl-3-aminopropylmethyldimethoxysilane, N-t-butyldimethylsilyl-N-methyl-3-aminopropyltriethoxysilane, N-t-butyldimethylsilyl-N-methyl-3-aminopropylmethyldiethoxysilane, N-t-butyldimethylsilyl-N-methyl-4-aminobutyltrimethoxysilane, N-t-butyldimethylsilyl-N-methyl-4-aminobutylmethyldimethoxysilane, N-t-butyldimethylsilyl-N-methyl-4-aminobutyltriethoxysilane, N-t-butyldimethylsilyl-N-methyl-4-aminobutylmethyldiethoxysilane, N-t-butyldimethylsilyl-N-ethylaminomethyltrimethoxysilane, N-t-butyldimethylsilyl-N-ethylaminomethylmethyldimethoxysilane, N-t-butyldimethylsilyl-N-ethylaminomethyltriethoxysilane, N-t-butyldimethylsilyl-N-ethylaminomethylmethyldiethoxysilane, N-t-butyldimethylsilyl-N-ethyl-2-aminoethyltrimethoxysilane, N-t-butyldimethylsilyl-N-ethyl-2-aminoethylmethyldimethoxysilane, N-t-butyldimethylsilyl-N-ethyl-2-aminoethyltriethoxysilane, N-t-butyldimethylsilyl-N-ethyl-2-aminoethylmethyldiethoxysilane, N-t-butyldimethylsilyl-N-ethyl-3-aminopropyltrimethoxysilane, N-t-butyldimethylsilyl-N-ethyl-3-aminopropylmethyldimethoxysilane, N-t-butyldimethylsilyl-N-ethyl-3-aminopropyltriethoxysilane, N-t-butyldimethylsilyl-N-ethyl-3-aminopropylmethyldiethoxysilane, N-t-butyldimethylsilyl-N-ethyl-4-aminobutyltrimethoxysilane, N-t-butyldimethylsilyl-N-ethyl-4-aminobutylmethyldimethoxysilane, N-t-butyldimethylsilyl-N-ethyl-4-aminobutyltriethoxysilane, N-t-butyldimethylsilyl-N-ethyl-4-aminobutylmethyldiethoxysilane, N-t-butyldimethylsilyl-N-butylaminomethyltrimethoxysilane, N-t-butyldimethylsilyl-N-butylaminomethylmethyldimethoxysilane, N-t-butyldimethylsilyl-N-butylaminomethyltriethoxysilane, N-t-butyldimethylsilyl-N-butylaminomethylmethyldiethoxysilane, N-t-butyldimethylsilyl-N-butyl-2-aminoethyltrimethoxysilane, N-t-butyldimethylsilyl-N-butyl-2-aminoethylmethyldimethoxysilane, N-t-butyldimethylsilyl-N-butyl-2-aminoethyltriethoxysilane, N-t-butyldimethylsilyl-N-butyl-2-aminoethylmethyldiethoxysilane, N-t-butyldimethylsilyl-N-butyl-3-aminopropyltrimethoxysilane, N-t-butyldimethylsilyl-N-butyl-3-aminopropylmethyldimethoxysilane, N-t-butyldimethylsilyl-N-butyl-3-aminopropyltriethoxysilane, N-t-butyldimethylsilyl-N-butyl-3-aminopropylmethyldiethoxysilane, N-t-butyldimethylsilyl-N-butyl-4-aminobutyltrimethoxysilane, N-t-butyldimethylsilyl-N-butyl-4-aminobutylmethyldimethoxysilane, N-t-butyldimethylsilyl-N-butyl-4-aminobutyltriethoxysilane, N-t-butyldimethylsilyl-N-butyl-4-aminobutylmethyldiethoxysilane, N-t-butyldimethylsilyl-N-cyclohexylaminomethyltrimethoxysilane, N-t-butyldimethylsilyl-N-cyclohexylaminomethylmethyldimethoxysilane, N-t-butyldimethylsilyl-N-cyclohexylaminomethyltriethoxysilane, N-t-butyldimethylsilyl-N-cyclohexylaminomethylmethyldiethoxysilane, N-t-butyldimethylsilyl-N-cyclohexyl-2-aminoethyltrimethoxysilane, N-t-butyldimethylsilyl-N-cyclohexyl-2-aminoethylmethyldimethoxysilane, N-t-butyldimethylsilyl-N-cyclohexyl-2-aminoethyltriethoxysilane, N-t-butyldimethylsilyl-N-cyclohexyl-2-aminoethylmethyldiethoxysilane, N-t-butyldimethylsilyl-N-cyclohexyl-3-aminopropyltrimethoxysilane, N-t-butyldimethylsilyl-N-cyclohexyl-3-aminopropylmethyldimethoxysilane, N-t-butyldimethylsilyl-N-cyclohexyl-3-aminopropyltriethoxysilane, N-t-butyldimethylsilyl-N-cyclohexyl-3-aminopropylmethyldiethoxysilane, N-t-butyldimethylsilyl-N-cyclohexyl-4-aminobutyltrimethoxysilane, N-t-butyldimethylsilyl-N-cyclohexyl-4-aminobutylmethyldimethoxysilane, N-t-butyldimethylsilyl-N-cyclohexyl-4-aminobutyltriethoxysilane, N-t-butyldimethylsilyl-N-cyclohexyl-4-aminobutylmethyldiethoxysilane, N-t-butyldimethylsilyl-N-phenylaminomethyltrimethoxysilane, N-t-butyldimethylsilyl-N-phenylaminomethylmethyldimethoxysilane, N-t-butyldimethylsilyl-N-phenylaminomethyltriethoxysilane, N-t-butyldimethylsilyl-N-phenylaminomethylmethyldiethoxysilane, N-t-butyldimethylsilyl-N-phenyl-2-aminoethyltrimethoxysilane, N-t-butyldimethylsilyl-N-phenyl-2-aminoethylmethyldimethoxysilane, N-t-butyldimethylsilyl-N-phenyl-2-aminoethyltriethoxysilane, N-t-butyldimethylsilyl-N-phenyl-2-aminoethylmethyldiethoxysilane, N-t-butyldimethylsilyl-N-phenyl-3-aminopropyltrimethoxysilane, N-t-butyldimethylsilyl-N-phenyl-3-aminopropylmethyldimethoxysilane, N-t-butyldimethylsilyl-N-phenyl-3-aminopropyltriethoxysilane, N-t-butyldimethylsilyl-N-phenyl-3-aminopropylmethyldiethoxysilane, N-t-butyldimethylsilyl-N-phenyl-4-aminobutyltrimethoxysilane, N-t-butyldimethylsilyl-N-phenyl-4-aminobutylmethyldimethoxysilane, N-t-butyldimethylsilyl-N-phenyl-4-aminobutyltriethoxysilane, N-t-butyldimethylsilyl-N-phenyl-4-aminobutylmethyldiethoxysilane, N-t-butyldimethylsilyl-N-benzylaminomethyltrimethoxysilane, N-t-butyldimethylsilyl-N-benzylaminomethylmethyldimethoxysilane, N-t-butyldimethylsilyl-N-benzylaminomethyltriethoxysilane, N-t-butyldimethylsilyl-N-benzylaminomethylmethyldiethoxysilane, N-t-butyldimethylsilyl-N-benzyl-2-aminoethyltrimethoxysilane, N-t-butyldimethylsilyl-N-benzyl-2-aminoethylmethyldimethoxysilane, N-t-butyldimethylsilyl-N-benzyl-2-aminoethyltriethoxysilane, N-t-butyldimethylsilyl-N-benzyl-2-aminoethylmethyldiethoxysilane, N-t-butyldimethylsilyl-N-benzyl-3-aminopropyltrimethoxysilane, N-t-butyldimethylsilyl-N-benzyl-3-aminopropylmethyldimethoxysilane, N-t-butyldimethylsilyl-N-benzyl-3-aminopropyltriethoxysilane, N-t-butyldimethylsilyl-N-benzyl-3-aminopropylmethyldiethoxysilane, N-t-butyldimethylsilyl-N-benzyl-4-aminobutyltrimethoxysilane, N-t-butyldimethylsilyl-N-benzyl-4-aminobutylmethyldimethoxysilane, N-t-butyldimethylsilyl-N-benzyl-4-aminobutyltriethoxysilane, N-t-butyldimethylsilyl-N-benzyl-4-aminobutylmethyldiethoxysilane, N-triisopropylsilyl-N-methylaminomethyltrimethoxysilane, N-triisopropylsilyl-N-methylaminomethylmethyldimethoxysilane, N-triisopropylsilyl-N-methylaminomethyltriethoxysilane, N-triisopropylsilyl-N-methylaminomethylmethyldiethoxysilane, N-triisopropylsilyl-N-methyl-2-aminoethyltrimethoxysilane, N-triisopropylsilyl-N-methyl-2-aminoethylmethyldimethoxysilane, N-triisopropylsilyl-N-methyl-2-aminoethyltriethoxysilane, N-triisopropylsilyl-N-methyl-2-aminoethylmethyldiethoxysilane, N-triisopropylsilyl-N-methyl-3-aminopropyltrimethoxysilane, N-triisopropylsilyl-N-methyl-3-aminopropylmethyldimethoxysilane, N-triisopropylsilyl-N-methyl-3-aminopropyltriethoxysilane, N-triisopropylsilyl-N-methyl-3-aminopropylmethyldiethoxysilane, N-triisopropylsilyl-N-methyl-4-aminobutyltrimethoxysilane, N-triisopropylsilyl-N-methyl-4-aminobutylmethyldimethoxysilane, N-triisopropylsilyl-N-methyl-4-aminobutyltriethoxysilane, N-triisopropylsilyl-N-methyl-4-aminobutylmethyldiethoxysilane, N-triisopropylsilyl-N-ethylaminomethyltrimethoxysilane, N-triisopropylsilyl-N-ethylaminomethylmethyldimethoxysilane, N-triisopropylsilyl-N-ethylaminomethyltriethoxysilane, N-triisopropylsilyl-N-ethylaminomethylmethyldiethoxysilane, N-triisopropylsilyl-N-ethyl-2-aminoethyltrimethoxysilane, N-triisopropylsilyl-N-ethyl-2-aminoethylmethyldimethoxysilane, N-triisopropylsilyl-N-ethyl-2-aminoethyltriethoxysilane, N-triisopropylsilyl-N-ethyl-2-aminoethylmethyldiethoxysilane, N-triisopropylsilyl-N-ethyl-3-aminopropyltrimethoxysilane, N-triisopropylsilyl-N-ethyl-3-aminopropylmethyldimethoxysilane, N-triisopropylsilyl-N-ethyl-3-aminopropyltriethoxysilane, N-triisopropylsilyl-N-ethyl-3-aminopropylmethyldiethoxysilane, N-triisopropylsilyl-N-ethyl-4-aminobutyltrimethoxysilane, N-triisopropylsilyl-N-ethyl-4-aminobutylmethyldimethoxysilane, N-triisopropylsilyl-N-ethyl-4-aminobutyltriethoxysilane, N-triisopropylsilyl-N-ethyl-4-aminobutylmethyldiethoxysilane, N-triisopropylsllyl-N-butylaminomethyltrimethoxysilane, N-triisopropylsilyl-N-butylaminomethylmethyldimethoxysilane, N-triisopropylsilyl-N-butylaminomethyltriethoxysilane, N-triisopropylsilyl-N-butylaminomethylmethyldiethoxysilane, N-triisopropylsilyl-N-butyl-2-aminoethyltrimethoxysilane, N-triisopropylsilyl-N-butyl-2-aminoethylmethyldimethoxysilane, N-triisopropylsilyl-N-butyl-2-aminoethyltriethoxysilane, N-triisopropylsilyl-N-butyl-2-aminoethylmethyldiethoxysilane, N-triisopropylsilyl-N-butyl-3-aminopropyltrimethoxysilane, N-triisopropylsilyl-N-butyl-3-aminopropylmethyldimethoxysilane, N-triisopropylsilyl-N-butyl-3-aminopropyltriethoxysilane, N-triisopropylsilyl-N-butyl-3-aminopropylmethyldiethoxysilane, N-triisopropylsilyl-N-butyl-4-aminobutyltrimethoxysilane, N-triisopropylsilyl-N-butyl-4-aminobutylmethyldimethoxysilane, N-triisopropylsilyl-N-butyl-4-aminobutyltriethoxysilane, N-triisopropylsilyl-N-butyl-4-aminobutylmethyldiethoxysilane, N-triisopropylsilyl-N-cyclohexylaminomethyltrimethoxysilane, N-triisopropylsilyl-N-cyclohexylaminomethylmethyldimethoxysilane, N-triisopropylsilyl-N-cyclohexylaminomethyltriethoxysilane, N-triisopropylsilyl-N-cyclohexylaminomethylmethyldiethoxysilane, N-triisopropylsilyl-N-cyclohexyl-2-aminoethyltrimethoxysilane, N-triisopropylsilyl-N-cyclohexyl-2-aminoethylmethyldimethoxysilane, N-triisopropylsilyl-N-cyclohexyl-2-aminoethyltriethoxysilane, N-triisopropylsilyl-N-cyclohexyl-2-aminoethylmethyldiethoxysilane, N-triisopropylsilyl-N-cyclohexyl-3-aminopropyltrimethoxysilane, N-triisopropylsilyl-N-cyclohexyl-3-aminopropylmethyldimethoxysilane, N-triisopropylsilyl-N-cyclohexyl-3-aminopropyltriethoxysilane, N-triisopropylsilyl-N-cyclohexyl-3-aminopropylmethyldiethoxysilane, N-triisopropylsilyl-N-cyclohexyl-4-aminobutyltrimethoxysilane, N-triisopropylsilyl-N-cyclohexyl-4-aminobutylmethyldimethoxysilane, N-triisopropylsilyl-N-cyclohexyl-4-aminobutyltriethoxysilane, N-triisopropylsilyl-N-cyclohexyl-4-aminobutylmethyldiethoxysilane, N-triisopropylsilyl-N-phenylaminomethyltrimethoxysilane, N-triisopropylsilyl-N-phenylaminomethylmethyldimethoxysilane, N-triisopropylsilyl-N-phenylaminomethyltriethoxysilane, N-triisopropylsilyl-N-phenylaminomethylmethyldiethoxysilane, N-triisopropylsilyl-N-phenyl-2-aminoethyltrimethoxysilane, N-triisopropylsilyl-N-phenyl-2-aminoethylmethyldimethoxysilane, N-triisopropylsilyl-N-phenyl-2-aminoethyltriethoxysilane, N-triisopropylsilyl-N-phenyl-2-aminoethylmethyldiethoxysilane, N-triisopropylsilyl-N-phenyl-3-aminopropyltrimethoxysilane, N-triisopropylsilyl-N-phenyl-3-aminopropylmethyldimethoxysilane, N-triisopropylsilyl-N-phenyl-3-aminopropyltriethoxysilane, N-triisopropylsilyl-N-phenyl-3-aminopropylmethyldiethoxysilane, N-triisopropylsilyl-N-phenyl-4-aminobutyltrimethoxysilane, N-triisopropylsilyl-N-phenyl-4-aminobutylmethyldimethoxysilane, N-triisopropylsilyl-N-phenyl-4-aminobutyltriethoxysilane, N-triisopropylsilyl-N-phenyl-4-aminobutylmethyldiethoxysilane, N-triisopropylsilyl-N-benzylaminomethyltrimethoxysilane, N-triisopropylsilyl-N-benzylaminomethylmethyldimethoxysilane, N-triisopropylsilyl-N-benzylaminomethyltriethoxysilane, N-triisopropylsilyl-N-benzylaminomethylmethyldiethoxysilane, N-triisopropylsilyl-N-benzyl-2-aminoethyltrimethoxysilane, N-triisopropylsilyl-N-benzyl-2-aminoethylmethyldimethoxysilane, N-triisopropylsilyl-N-benzyl-2-aminoethyltriethoxysilane, N-triisopropylsilyl-N-benzyl-2-aminoethylmethyldiethoxysilane, N-triisopropylsilyl-N-benzyl-3-aminopropyltrimethoxysilane, N-triisopropylsilyl-N-benzyl-3-aminopropylmethyldimethoxysilane, N-triisopropylsilyl-N-benzyl-3-aminopropyltriethoxysilane, N-triisopropylsilyl-N-benzyl-3-aminopropylmethyldiethoxysilane, N-triisopropylsilyl-N-benzyl-4-aminobutyltrimethoxysilane, N-triisopropylsilyl-N-benzyl-4-aminobutylmethyldimethoxysilane, N-triisopropylsilyl-N-benzyl-4-aminobutyltriethoxysilane, N-triisopropylsilyl-N-benzyl-4-aminobutylmethyldiethoxysilane, etc.

Of these, preferred are those of formula (1) wherein $R^1$ is t-butyl which is typical of the substituted or unsubstituted, secondary or tertiary, monovalent hydrocarbon group of 3 to 20 carbon atoms, specifically, N-t-butyldimethylsilyl-N-methylaminomethyltrimethoxysilane, N-t-butyldimethylsilyl-N-methylaminomethylmethyldimethoxysilane, N-t-butyldimethylsilyl-N-methylaminomethyltriethoxysilane, N-t-butyldimethylsilyl-N-methylaminomethylmethyldiethoxysilane, N-t-butyldimethylsilyl-N-methyl-2-aminoethyltrimethoxysilane, N-t-butyldimethylsilyl-N-methyl-2-aminoethylmethyldimethoxysilane, N-t-butyldimethylsilyl-N-methyl-2-aminoethyltriethoxysilane, N-t-butyldimethylsilyl-N-methyl-2-aminoethylmethyldiethoxysilane, N-t-butyldimethylsilyl-N-methyl-3-aminopropyltrimethoxysilane, N-t-butyldimethylsilyl-N-methyl-3-aminopropylmethyldimethoxysilane, N-t-butyldimethylsilyl-N-methyl-3-aminopropyltriethoxysilane, N-t-butyldimethylsilyl-N-methyl-3-aminopropylmethyldiethoxysilane, N-t-butyldimethylsilyl-N-methyl-4-aminobutyltrimethoxysilane, N-t-butyldimethylsilyl-N-methyl-4-aminobutylmethyldimethoxysilane, N-t-butyldimethylsilyl-N-methyl-4-aminobutyltriethoxysilane, N-t-butyldimethylsilyl-N-methyl-4-aminobutylmethyldiethoxysilane, N-t-butyldimethylsilyl-N-ethylaminomethyltrimethoxysilane, N-t-butyldimethylsilyl-N-ethylaminomethylmethyldimethoxysilane, N-t-butyldimethylsilyl-N-ethylaminomethyltriethoxysilane, N-t-butyldimethylsilyl-N-ethylaminomethylmethyldiethoxysilane, N-t-butyldimethylsilyl-N-ethyl-2-aminoethyltrimethoxysilane, N-t-butyldimethylsilyl-N-ethyl-2-aminoethylmethyldimethoxysilane, N-t-butyldimethylsilyl-N-ethyl-2-aminoethyltriethoxysilane, N-t-butyldimethylsilyl-N-ethyl-2-aminoethylmethyldiethoxysilane, N-t-butyldimethylsilyl-N-ethyl-3-aminopropyltrimethoxysilane, N-t-butyldimethylsilyl-N-ethyl-3-aminopropylmethyldimethoxysilane, N-t-butyldimethylsilyl-N-ethyl-3-aminopropyltriethoxysilane, N-t-butyldimethylsilyl-N-ethyl-3-aminopropylmethyldiethoxysilane, N-t-butyldimethylsilyl-N-ethyl-4-aminobutyltrimethoxysilane, N-t-butyldimethylsilyl-N-ethyl-4-aminobutylmethyldimethoxysilane, N-t-butyldimethylsilyl-N-ethyl-4-aminobutyltriethoxysilane, N-t-butyldimethylsilyl-N-ethyl-4-aminobutylmethyldiethoxysilane, N-t-butyldimethylsilyl-N-butylaminomethyltrimethoxysilane, N-t-butyldimethylsilyl-N-butylaminomethylmethyldimethoxysilane, N-t-butyldimethylsilyl-N-butylaminomethyltriethoxysilane, N-t-butyldimethylsilyl-N-butylaminomethylmethyldiethoxysilane, N-t-butyldimethylsilyl-N-butyl-2-aminoethyltrimethoxysilane, N-t-butyldimethylsilyl-N-butyl-2-aminoethylmethyldimethoxysilane, N-t-butyldimethylsilyl-N-butyl-2-aminoethyltriethoxysilane, N-t-butyldimethylsilyl-N-butyl-2-aminoethylmethyldiethoxysilane, N-t-butyldimethylsilyl-N-butyl-3-aminopropyltrimethoxysilane, N-t-butyldimethylsilyl-N-butyl-3-aminopropylmethyldimethoxysilane, N-t-butyldimethylsilyl-N-butyl-3-aminopropyltriethoxysilane, N-t-butyldimethylsilyl-N-butyl-3-aminopropylmethyldiethoxysilane, N-t-butyldimethylsilyl-N-butyl-4-aminobutyltrimethoxysilane, N-t-butyldimethylsilyl-N-butyl-4-aminobutylmethyldimethoxysilane, N-t-butyldimethylsilyl-N-butyl-4-aminobutyltriethoxysilane, N-t-butyldimethylsilyl-N-butyl-4-aminobutylmethyldiethoxysilane, N-t-butyldimethylsilyl-N-cyclohexylaminomethyltrimethoxysilane, N-t-butyldimethylsilyl-N-cyclohexylaminomethylmethyldimethoxysilane, N-t-butyldimethylsilyl-N-cyclohexylaminomethyltriethoxysilane, N-t-butyldimethylsilyl-N-cyclohexylaminomethylmethyldiethoxysilane, N-t-butyldimethylsilyl-N-cyclohexyl-2-aminoethyltrimethoxysilane, N-t-butyldimethylsilyl-N-cyclohexyl-2-aminoethylmethyldimethoxysilane, N-t-butyldimethylsilyl-N-cyclohexyl-2-aminoethyltriethoxysilane, N-t-butyldimethylsilyl-N-cyclohexyl-2-aminoethylmethyldiethoxysilane, N-t-butyldimethylsilyl-N-cyclohexyl-3-aminopropyltrimethoxysilane, N-t-butyldimethylsilyl-N-cyclohexyl-3-aminopropylmethyldimethoxysilane, N-t-butyldimethylsilyl-N-cyclohexyl-3-aminopropyltriethoxysilane, N-t-butyldimethylsilyl-N-cyclohexyl-3-aminopropylmethyldiethoxysilane, N-t-butyldimethylsilyl-N-cyclohexyl-4-aminobutyltrimethoxysilane, N-t-butyldimethylsilyl-N-cyclohexyl-4-aminobutylmethyldimethoxysilane, N-t-butyldimethylsilyl-N-cyclohexyl-4-aminobutyltriethoxysilane, N-t-butyldimethylsilyl-N-cyclohexyl-4-aminobutylmethyldiethoxysilane, N-t-butyldimethylsilyl-N-phenylaminomethyltrimethoxysilane, N-t-butyldimethylsilyl-N-phenylaminomethylmethyldimethoxysilane, N-t-butyldimethylsilyl-N-phenylaminomethyltriethoxysilane, N-t-butyldimethylsilyl-N-phenylaminomethylmethyldiethoxysilane, N-t-butyldimethylsilyl-N-phenyl-2-aminoethyltrimethoxysilane, N-t-butyldimethylsilyl-N-phenyl-2-aminoethylmethyldimethoxysilane, N-t-butyldimethylsilyl-N-phenyl-2-aminoethyltriethoxysilane, N-t-butyldimethylsilyl-N-phenyl-2-aminoethylmethyldiethoxysilane, N-t-butyldimethylsilyl-N-phenyl-3-aminopropyltrimethoxysilane, N-t-butyldimethylsilyl-N-phenyl-3-aminopropylmethyldimethoxysilane, N-t-butyldimethylsilyl-N-phenyl-3-aminopropyltriethoxysilane, N-t-butyldimethylsilyl-N-phenyl-3-aminopropylmethyldiethoxysilane, N-t-butyldimethylsilyl-N-phenyl-4-aminobutyltrimethoxysilane, N-t-butyldimethylsilyl-N-phenyl-4-aminobutylmethyldimethoxysilane, N-t-butyldimethylsilyl-N-phenyl-4-aminobutyltriethoxysilane, N-t-butyldimethylsilyl-N-phenyl-4-aminobutylmethyldiethoxysilane, N-t-butyldimethylsilyl-N-benzylaminomethyltrimethoxysilane, N-t-butyldimethylsilyl-N-benzylaminomethylmethyldimethoxysilane, N-t-butyldimethylsilyl-N-benzylaminomethyltriethoxysilane, N-t-butyldimethylsilyl-N-benzylaminomethylmethyldiethoxysilane, N-t-butyldimethylsilyl-N-benzyl-2-aminoethyltrimethoxysilane, N-t-butyldimethylsilyl-N-benzyl-2-aminoethylmethyldimethoxysilane, N-t-butyldimethylsilyl-N-benzyl-2-aminoethyltriethoxysilane, N-t-butyldimethylsilyl-N-benzyl-2-aminoethylmethyldiethoxysilane, N-t-butyldimethylsilyl-N-benzyl-3-aminopropyltrimethoxysilane, N-t-butyldimethylsilyl-N-benzyl-3-aminopropylmethyldimethoxysilane, N-t-butyldimethylsilyl-N-benzyl-3-aminopropyltriethoxysilane, N-t-butyldimethylsilyl-N-benzyl-3-aminopropylmethyldiethoxysilane, N-t-butyldimethylsilyl-N-benzyl-4-aminobutyltrimethoxysilane, N-t-butyldimethylsilyl-N-benzyl-4-aminobutylmethyldimethoxysilane, N-t-butyldimethylsilyl-N-benzyl-4-aminobutyltriethoxysilane, and N-t-butyldimethylsilyl-N-benzyl-4-aminobutylmethyldiethoxysilane.

Also preferred are those of formula (1) wherein $R^1$, $R^2$ and $R^3$ are isopropyl which is typical of the substituted or unsubstituted, monovalent hydrocarbon group of 2 to 20 carbon atoms, specifically, N-triisopropylsilyl-N-methylaminomethyltrimethoxysilane, N-triisopropylsilyl-N-methylaminomethylmethyldimethoxysilane, N-triisopropylsilyl-N-methylaminomethyltriethoxysilane, N-triisopropylsilyl-N-methylaminomethylmethyldiethoxysilane, N-triisopropylsilyl-N-methyl-2-aminoethyltrimethoxysilane, N-triisopropylsilyl-N-methyl-2-aminoethylmethyldimethoxysilane, N-triisopropylsilyl-N-methyl-2-aminoethyltriethoxysilane, N-triisopropylsilyl-N-methyl-2-aminoethylmethyldiethoxysilane, N-triisopropylsilyl-N-methyl-3-aminopropyltrimethoxysilane, N-triisopropylsilyl-N-methyl-3-aminopropylmethyldimethoxysilane, N-triisopropylsilyl-N-methyl-3-aminopropyltriethoxysilane, N-triisopropylsilyl-N-methyl-3-aminopropylmethyldiethoxysilane, N-triisopropylsilyl-N-methyl-4-aminobutyltrimethoxysilane, N-triisopropylsilyl-N-methyl-4-aminobutylmethyldimethoxysilane, N-triisopropylsilyl-N-methyl-4-aminobutyltriethoxysilane, N-triisopropylsilyl-N-methyl-4-aminobutylmethyldiethoxysilane, N-triisopropylsilyl-N-ethylaminomethyltrimethoxysilane, N-triisopropylsilyl-N-ethylaminomethylmethyldimethoxysilane, N-triisopropylsilyl-N-ethylaminomethyltriethoxysilane, N-triisopropylsilyl-N-ethylaminomethylmethyldiethoxysilane, N-triisopropylsilyl-N-ethyl-2-aminoethyltrimethoxysilane, N-triisopropylsilyl-N-ethyl-2-aminoethylmethyldimethoxysilane, N-triisopropylsilyl-N-ethyl-2-aminoethyltriethoxysilane, N-triisopropylsilyl-N-ethyl-2-aminoethylmethyldiethoxysilane, N-triisopropylsilyl-N-ethyl-3-aminopropyltrimethoxysilane, N-triisopropylsilyl-N-ethyl-3-aminopropylmethyldimethoxysilane, N-triisopropylsilyl-N-ethyl-3-aminopropyltriethoxysilane, N-triisopropylsilyl-N-ethyl-3-aminopropylmethyldiethoxysilane, N-triisopropylsilyl-N-ethyl-4-aminobutyltrimethoxysilane, N-triisopropylsilyl-N-ethyl-4-aminobutylmethyldimethoxysilane, N-triisopropylsilyl-N-ethyl-4-aminobutyltriethoxysilane, N-triisopropylsilyl-N-ethyl-4-aminobutylmethyldiethoxysilane, N-triisopropylsilyl-N-butylaminomethyltrimethoxysilane, N-triisopropylsilyl-N-butylaminomethylmethyldimethoxysilane, N-triisopropylsilyl-N-butylaminomethyltriethoxysilane, N-triisopropylsilyl-N-butylaminomethylmethyldiethoxysilane, N-triisopropylsilyl-N-butyl-2-aminoethyltrimethoxysilane, N-triisopropylsilyl-N-butyl-2-aminoethylmethyldimethoxysilane, N-triisopropylsilyl-N-butyl-2-aminoethyltriethoxysilane, N-triisopropylsilyl-N-butyl-2-aminoethylmethyldiethoxysilane, N-triisopropylsilyl-N-butyl-3-aminopropyltrimethoxysilane, N-triisopropylsilyl-N-butyl-3-aminopropylmethyldimethoxysilane, N-triisopropylsilyl-N-butyl-3-aminopropyltriethoxysilane, N-triisopropylsilyl-N-butyl-3-aminopropylmethyldiethoxysilane, N-triisopropylsilyl-N-butyl-4-aminobutyltrimethoxysilane, N-triisopropylsilyl-N-butyl-4-aminobutylmethyldimethoxysilane, N-triisopropylsilyl-N-butyl-4-aminobutyltriethoxysilane, N-triisopropylsilyl-N-butyl-4-aminobutylmethyldiethoxysilane, N-triisopropylsilyl-N-cyclohexylaminomethyltrimethoxysilane, N-triisopropylsilyl-N-cyclohexylaminomethylmethyldimethoxysilane, N-triisopropylsilyl-N-cyclohexylaminomethyltriethoxysilane, N-triisopropylsilyl-N-cyclohexylaminomethylmethyldiethoxysilane, N-triisopropylsilyl-N-cyclohexyl-2-aminoethyltrimethoxysilane, N-triisopropylsilyl-N-cyclohexyl-2-aminoethylmethyldimethoxysilane, N-triisopropylsilyl-N-cyclohexyl-2-aminoethyltriethoxysilane, N-triisopropylsilyl-N-cyclohexyl-2-aminoethylmethyldiethoxysilane, N-triisopropylsilyl-N-cyclohexyl-3-aminopropyltrimethoxysilane, N-triisopropylsilyl-N-cyclohexyl-3-aminopropylmethyldimethoxysilane, N-triisopropylsilyl-N-cyclohexyl-3-aminopropyltriethoxysilane, N-triisopropylsilyl-N-cyclohexyl-3-aminopropylmethyldiethoxysilane, N-triisopropylsilyl-N-cyclohexyl-4-aminobutyltrimethoxysilane, N-triisopropylsilyl-N-cyclohexyl-4-aminobutylmethyldimethoxysilane, N-triisopropylsilyl-N-cyclohexyl-4-aminobutyltriethoxysilane, N-triisopropylsilyl-N-cyclohexyl-4-aminobutylmethyldiethoxysilane, N-triisopropylsilyl-N-phenylaminomethyltrimethoxysilane, N-triisopropylsilyl-N-phenylaminomethylmethyldimethoxysilane, N-triisopropylsilyl-N-phenylaminomethyltriethoxysilane, N-triisopropylsilyl-N-phenylaminomethylmethyldiethoxysilane, N-triisopropylsilyl-N-phenyl-2-aminoethyltrimethoxysilane, N-triisopropylsilyl-N-phenyl-2-aminoethylmethyldimethoxysilane, N-triisopropylsilyl-N-phenyl-2-aminoethyltriethoxysilane, N-triisopropylsilyl-N-phenyl-2-aminoethylmethyldiethoxysilane, N-triisopropylsilyl-N-phenyl-3-aminopropyltrimethoxysilane, N-triisopropylsilyl-N-phenyl-3-aminopropylmethyldimethoxysilane, N-triisopropylsilyl-N-phenyl-3-aminopropyltriethoxysilane, N-triisopropylsilyl-N-phenyl-3-aminopropylmethyldiethoxysilane, N-triisopropylsilyl-N-phenyl-4-aminobutyltrimethoxysilane, N-triisopropylsilyl-N-phenyl-4-aminobutylmethyldimethoxysilane, N-triisopropylsilyl-N-phenyl-4-aminobutyltriethoxysilane, N-triisopropylsilyl-N-phenyl-4-aminobutylmethyldiethoxysilane, N-triisopropylsilyl-N-benzylaminomethyltrimethoxysilane, N-triisopropylsilyl-N-benzylaminomethylmethyldimethoxysilane, N-triisopropylsilyl-N-benzylaminomethyltriethoxysilane, N-triisopropylsilyl-N-benzylaminomethylmethyldiethoxysilane, N-triisopropylsilyl-N-benzyl-2-aminoethyltrimethoxysilane, N-triisopropylsilyl-N-benzyl-2-aminoethylmethyldimethoxysilane, N-triisopropylsilyl-N-benzyl-2-aminoethyltriethoxysilane, N-triisopropylsilyl-N-benzyl-2-aminoethylmethyldiethoxysilane, N-triisopropylsilyl-N-benzyl-3-aminopropyltrimethoxysilane, N-triisopropylsilyl-N-benzyl-3-aminopropylmethyldimethoxysilane, N-triisopropylsilyl-N-benzyl-3-aminopropyltriethoxysilane, N-triisopropylsilyl-N-benzyl-3-aminopropylmethyldiethoxysilane, N-triisopropylsilyl-N-benzyl-4-aminobutyltrimethoxysilane, N-triisopropylsilyl-N-benzyl-4-aminobutylmethyldimethoxysilane, N-triisopropylsilyl-N-benzyl-4-aminobutyltriethoxysilane, and N-triisopropylsilyl-N-benzyl-4-aminobutylmethyldiethoxysilane.

In another embodiment, the organoxysilane compound having a silyl-protected secondary amino group represented by formula (1) is prepared by reacting a compound having the general formula (2) with a hydrogensilane compound having the general formula (3) in the presence of a platinum catalyst.

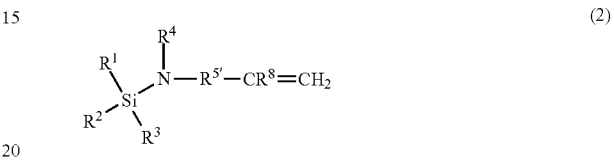

(2)

Herein $R^1$, $R^2$, $R^3$, and $R^4$ are as defined above, $R^8$ is hydrogen or methyl, $R^{5'}$ is a straight or branched divalent hydrocarbon group of 1 to 18 carbon atoms when $R^8$ is hydrogen, or $R^{5'}$ is a straight or branched divalent hydrocarbon group of 1 to 17 carbon atoms when $R^8$ is methyl.

(3)

Herein $R^6$ and $R^7$ each are a substituted or unsubstituted, monovalent hydrocarbon group of 1 to 20 carbon atoms, and n is 0 or 1.

In formula (2), when $R^8$ is hydrogen, $R^{5'}$ is a straight or branched divalent hydrocarbon group of 1 to 18 carbon atoms. When $R^8$ is methyl, $R^{5'}$ is a straight or branched divalent hydrocarbon group of 1 to 17 carbon atoms. Suitable hydrocarbon groups include alkylene groups such as methylene, dimethylene, trimethylene, tetramethylene, hexamethylene, octamethylene, decamethylene, and isobutylene, arylene groups such as phenylene, and aralkylene groups such as methylenephenylene and methylenephenylenemethylene.

Examples of the compound having formula (2) include N-triethylsilyl-N-methyl-N-allylamine, N-triethylsilyl-N-methyl-N-methallylamine, N-triethylsilyl-N-methyl-N-butenylamine, N-triethylsilyl-N-ethyl-N-allylamine, N-triethylsilyl-N-ethyl-N-methallylamine, N-triethylsilyl-N-ethyl-N-butenylamine, N-triethylsilyl-N-butyl-N-allylamine, N-triethylsilyl-N-butyl-N-methallylamine, N-triethylsilyl-N-butyl-N-butenylamine, N-triethylsilyl-N-cyclohexyl-N-allylamine, N-triethylsilyl-N-cyclohexyl-N-methallylamine, N-triethylsilyl-N-cyclohexyl-N-butenylamine, N-triethylsilyl-N-phenyl-N-allylamine, N-triethylsilyl-N-phenyl-N-methallylamine, N-triethylsilyl-N-phenyl-N-butenylamine, N-triethylsilyl-N-benzyl-N-allylamine, N-triethylsilyl-N-benzyl-N-methallylamine, N-triethylsilyl-N-benzyl-N-butenylamine, N-t-butyldimethylsilyl-N-methyl-N-allylamine, N-t-butyldimethylsilyl-N-methyl-N-methallylamine, N-t-butyldimethylsilyl-N-methyl-N-butenylamine, N-t-butyldimethylsilyl-N-ethyl-N-allylamine, N-t-butyldimethylsilyl-N-ethyl-N-methallylamine, N-t-butyldimethylsilyl-N-ethyl-N-butenylamine, N-t-butyldimethylsilyl-N-butyl-N-allylamine, N-t-butyldimethylsilyl-N-butyl-N-methallylamine, N-t-butyldimethylsilyl-N-butyl-N-butenylamine, N-t-butyldimethylsilyl-N-cyclohexyl-N-allylamine, N-t-butyldimethylsilyl-N-cyclohexyl-N-methallylamine, N-t-butyldimethylsilyl-N-cyclohexyl-N-butenylamine, N-t- butyldimethylsilyl-N-phenyl-N-allylamine, N-t-butyldimethylsilyl-N-phenyl-N-methallylamine, N-t-butyldimethylsilyl-N-phenyl-N-butenylamine, N-t-butyldimethylsilyl-N-benzyl-N-allylamine, N-t-butyldimethylsilyl-N-benzyl-N-methallylamine, N-t-butyldimethylsilyl-N-benzyl-N-butenylamine, N-triisopropylsilyl-N-methyl-N-allylamine, N-triisopropylsilyl-N-methyl-N-methallylamine, N-triisopropylsilyl-N-methyl-N-butenylamine, N-triisopropylsilyl-N-ethyl-N-allylamine, N-triisopropylsilyl-N-ethyl-N-methallylamine, N-triisopropylsilyl-N-ethyl-N-butenylamine, N-triisopropylsilyl-N-butyl-N-allylamine, N-triisopropylsilyl-N-butyl-N-methallylamine, N-triisopropylsilyl-N-butyl-N-butenylamine, N-triisopropylsilyl-N-cyclohexyl-N-allylamine, N-triisopropylsilyl-N-cyclohexyl-N-methallylamine, N-triisopropylsilyl-N-cyclohexyl-N-butenylamine, N-triisopropylsilyl-N-phenyl-N-allylamine, N-triisopropylsilyl-N-phenyl-N-methallylamine, N-triisopropylsilyl-N-phenyl-N-butenylamine, N-triisopropylsilyl-N-benzyl-N-allylamine, N-triisopropylsilyl-N-benzyl-N-methallylamine, N-triisopropylsilyl-N-benzyl-N-butenylamine, etc.

Examples of the hydrogensilane compound having formula (3) include trimethoxysilane, methyldimethoxysilane, triethoxysilane, and methyldiethoxysilane.

Although the compound of formula (2) and the hydrogensilane compound of formula (3) may be used in any desired ratio, it is preferred for reactivity and productivity to use 0.5 to 2 moles, especially 0.8 to 1.2 moles of the hydrogensilane compound of formula (3) per mole of the compound of formula (2).

Suitable platinum catalysts used herein include chloroplatinic acid, chloroplatinic acid in alcohol, platinum/1,3-divinyl-1,1,3,3-tetramethyldisiloxane complex in toluene or xylene, tetrakis(triphenylphosphine)platinum, dichlorobis(triphenylphosphine)platinum, dichlorobis(acetonitrile)platinum, dichlorobis(benzonitrile)platinum, dichloro(cyclooctadiene)platinum, and platinum on active carbon.

Although the amount of the catalyst used is not particularly limited, it is preferred for reactivity and productivity to use 0.000001 to 0.01 mole, especially 0.00001 to 0.001 mole of the catalyst per mole of the compound of formula (2).

Although the reaction temperature is not particularly limited, a temperature in the range of 0 to 120° C., especially 20 to 100° C. is preferred. Although the reaction time is not particularly limited, a time in the range of 1 to 40 hours, especially 1 to 20 hours is preferred.

Although the reaction may take place in a solventless system, a solvent may be used. Suitable solvents include hydrocarbon solvents such as pentane, hexane, cyclohexane, heptane, isooctane, benzene, toluene and xylene, ether solvents such as diethyl ether, tetrahydrofuran, and dioxane, ester solvents such as ethyl acetate and butyl acetate, aprotic polar solvents such as acetonitrile, N,N-dimethylformamide, and N-methylpyrrolidone, and chlorinated hydrocarbon solvents such as dichloromethane and chloroform, which may be used alone or in admixture of two or more.

In another embodiment, the organoxysilane compound having a silyl-protected secondary amino group represented by formula (1) is prepared by silylating a compound having the general formula (4) with a silylating agent having a $R^1R^2R^3Si-$ group.

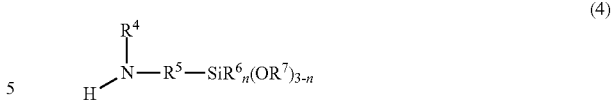

(4)

In formula (4), $R^4$, $R^6$ and $R^7$ each are a substituted or unsubstituted, monovalent hydrocarbon group of 1 to 20 carbon atoms, $R^5$ is a straight or branched divalent hydrocarbon group of 1 to 20 carbon atoms, and n is 0 or 1. In the $R^1R^2R^3Si-$ group, $R^1$, $R^2$ and $R^3$ each are a substituted or unsubstituted, monovalent hydrocarbon group of 1 to 20 carbon atoms.

Examples of the compound having formula (4) include N-methylaminomethyltrimethoxysilane, N-methylaminomethylmethyldimethoxysilane, N-methylaminomethyltriethoxysilane, N-methylaminomethylmethyldiethoxysilane, N-methyl-2-aminoethyltrimethoxysilane, N-methyl-2-aminoethylmethyldimethoxysilane, N-methyl-2-aminoethyltriethoxysilane, N-methyl-2-aminoethylmethyldiethoxysilane, N-methyl-3-aminopropyltrimethoxysilane, N-methyl-3-aminopropylmethyldimethoxysilane, N-methyl-3-aminopropyltriethoxysilane, N-methyl-3-aminopropylmethyldiethoxysilane, N-methyl-4-aminobutyltrimethoxysilane, N-methyl-4-aminobutylmethyldimethoxysilane, N-methyl-4-aminobutyltriethoxysilane, N-methyl-4-aminobutylmethyldiethoxysilane, N-ethylaminomethyltrimethoxysilane, N-ethylaminomethylmethyldimethoxysilane, N-ethylaminomethyltriethoxysilane, N-ethylaminomethylmethyldiethoxysilane, N-ethyl-2-aminoethyltrimethoxysilane, N-ethyl-2-aminoethylmethyldimethoxysilane, N-ethyl-2-aminoethyltriethoxysilane, N-ethyl-2-aminoethylmethyldiethoxysilane, N-ethyl-3-aminopropyltrimethoxysilane, N-ethyl-3-aminopropylmethyldimethoxysilane, N-ethyl-3-aminopropyltriethoxysilane, N-ethyl-3-aminopropylmethyldiethoxysilane, N-ethyl-4-aminobutyltrimethoxysilane, N-ethyl-4-aminobutylmethyldimethoxysilane, N-ethyl-4-aminobutyltriethoxysilane, N-ethyl-4-aminobutylmethyldiethoxysilane, N-butylaminomethyltrimethoxysilane, N-butylaminomethylmethyldimethoxysilane, N-butylaminomethyltriethoxysilane, N-butylaminomethylmethyldiethoxysilane, N-butyl-2-aminoethyltrimethoxysilane, N-butyl-2-aminoethylmethyldimethoxysilane, N-butyl-2-aminoethyltriethoxysilane, N-butyl-2-aminoethylmethyldiethoxysilane, N-butyl-3-aminopropyltrimethoxysilane, N-butyl-3-aminopropylmethyldimethoxysilane, N-butyl-3-aminopropyltriethoxysilane, N-butyl-3-aminopropylmethyldiethoxysilane, N-butyl-4-aminobutyltrimethoxysilane, N-butyl-4-aminobutylmethyldimethoxysilane, N-butyl-4-aminobutyltriethoxysilane, N-butyl-4-aminobutylmethyldiethoxysilane, N-cyclohexylaminomethyltrimethoxysilane, N-cyclohexylaminomethylmethyldimethoxysilane, N-cyclohexylaminomethyltriethoxysilane, N-cyclohexylaminomethylmethyldiethoxysilane, N-cyclohexyl-2-aminoethyltrimethoxysilane, N-cyclohexyl-2-aminoethylmethyldimethoxysilane, N-cyclohexyl-2-aminoethyltriethoxysilane, N-cyclohexyl-2-aminoethylmethyldiethoxysilane, N-cyclohexyl-3-aminopropyltrimethoxysilane, N-cyclohexyl-3-aminopropylmethyldimethoxysilane, N-cyclohexyl-3-aminopropyltriethoxysilane, N-cyclohexyl-3-aminopropylmethyldiethoxysilane, N-cyclohexyl-4-aminobutyltrimethoxysilane, N-cyclohexyl-4- aminobutylmethyldimethoxysilane, N-cyclohexyl-4-aminobutyltriethoxysilane, N-cyclohexyl-4-aminobutylmethyldiethoxysilane, N-phenylaminomethyltrimethoxysilane, N-phenylaminomethylmethyldimethoxysilane, N-phenylaminomethyltriethoxysilane, N-phenylaminomethylmethyldiethoxysilane, N-phenyl-2-aminoethyltrimethoxysilane, N-phenyl-2-aminoethylmethyldimethoxysilane, N-phenyl-2-aminoethyltriethoxysilane, N-phenyl-2-aminoethylmethyldiethoxysilane, N-phenyl-3-aminopropyltrimethoxysilane, N-phenyl-3-aminopropylmethyldimethoxysilane, N-phenyl-3-aminopropyltriethoxysilane, N-phenyl-3-aminopropylmethyldiethoxysilane, N-phenyl-4-aminobutyltrimethoxysilane, N-phenyl-4-aminobutylmethyldimethoxysilane, N-phenyl-4-aminobutyltriethoxysilane, N-phenyl-4-aminobutylmethyldiethoxysilane, N-benzylaminomethyltrimethoxysilane, N-benzylaminomethylmethyldimethoxysilane, N-benzylaminomethyltriethoxysilane, N-benzylaminomethylmethyldiethoxysilane, N-benzyl-2-aminoethyltrimethoxysilane, N-benzyl-2-aminoethylmethyldimethoxysilane, N-benzyl-2-aminoethyltriethoxysilane, N-benzyl-2-aminoethylmethyldiethoxysilane, N-benzyl-3-aminopropyltrimethoxysilane, N-benzyl-3-aminopropylmethyldimethoxysilane, N-benzyl-3-aminopropyltriethoxysilane, N-benzyl-3-aminopropylmethyldiethoxysilane, N-benzyl-4-aminobutyltrimethoxysilane, N-benzyl-4-aminobutylmethyldimethoxysilane, N-benzyl-4-aminobutyltriethoxysilane, N-benzyl-4-aminobutylmethyldiethoxysilane, etc.

Suitable silylating agents used herein include triorganohalosilanes of the formula: $R^1R^2R^3SiX$ (wherein $R^1$, $R^2$ and $R^3$ are as defined above and X is a halogen, typically chlorine) such as triethylchlorosilane, triethylbromosilane, triethyliodosilane, t-butyldimethylchlorosilane, and triisopropylchlorosilane, disilazanes of the formula: $(R^1R^2R^3Si)_2NH$ (wherein $R^1$, $R^2$ and $R^3$ are as defined above) such as hexaethyldisilazane, other silazane compounds, and silyltrifluoromethanesulfonic acids such as triethylsilyltrifluoromethanesulfonic acid, t-butyldimethylsilyltrifluoromethanesulfonic acid, and triisopropylsilyltrifluoromethanesulfonic acid.

Although the compound of formula (4) and the silylating agent may be used in any desired ratio, it is preferred for reactivity and productivity to use 0.5 to 4 moles, especially 0.8 to 2 moles of the silylating agent per mole of the compound of formula (4).

Although the reaction temperature is not particularly limited, a temperature in the range of 0 to 200° C., especially 20 to 150° C. is preferred. Although the reaction time is not particularly limited, a time in the range of 1 to 40 hours, especially 1 to 20 hours is preferred.

Although the reaction may take place in a solventless system, a solvent may be used. Suitable solvents include hydrocarbon solvents such as pentane, hexane, cyclohexane, heptane, isooctane, benzene, toluene and xylene, ether solvents such as diethyl ether, tetrahydrofuran, and dioxane, ester solvents such as ethyl acetate and butyl acetate, aprotic polar solvents such as acetonitrile, N,N-dimethylformamide, and N-methylpyrrolidone, and chlorinated hydrocarbon solvents such as dichloromethane and chloroform, which may be used alone or in admixture of two or more.

EXAMPLE

Examples of the invention are given below by way of illustration and not by way of limitation.

Example 1

N-t-butyldimethylsilyl-N-butyl-3-aminopropyltrimethoxysilane

A flask equipped with a stirrer, reflux condenser, dropping funnel and thermometer was charged with 22.8 g (0.1 mol) of N-t-butyldimethylsilyl-N-butyl-N-allylamine and 0.07 g of a toluene solution of platinum/1,3-divinyl-1,1,3,3-tetramethyldisiloxane complex (Pt concentration 3 wt %) and heated at 50° C. Once the internal temperature became steady, 12.2 g (0.1 mol) of trimethoxysilane was added dropwise over 1 hour. Stirring was continued at the temperature for a further 1 hour. The reaction solution was distilled, collecting 27.3 g of a fraction having a boiling point of 128-129° C./0.4 kPa.

Figure 2:
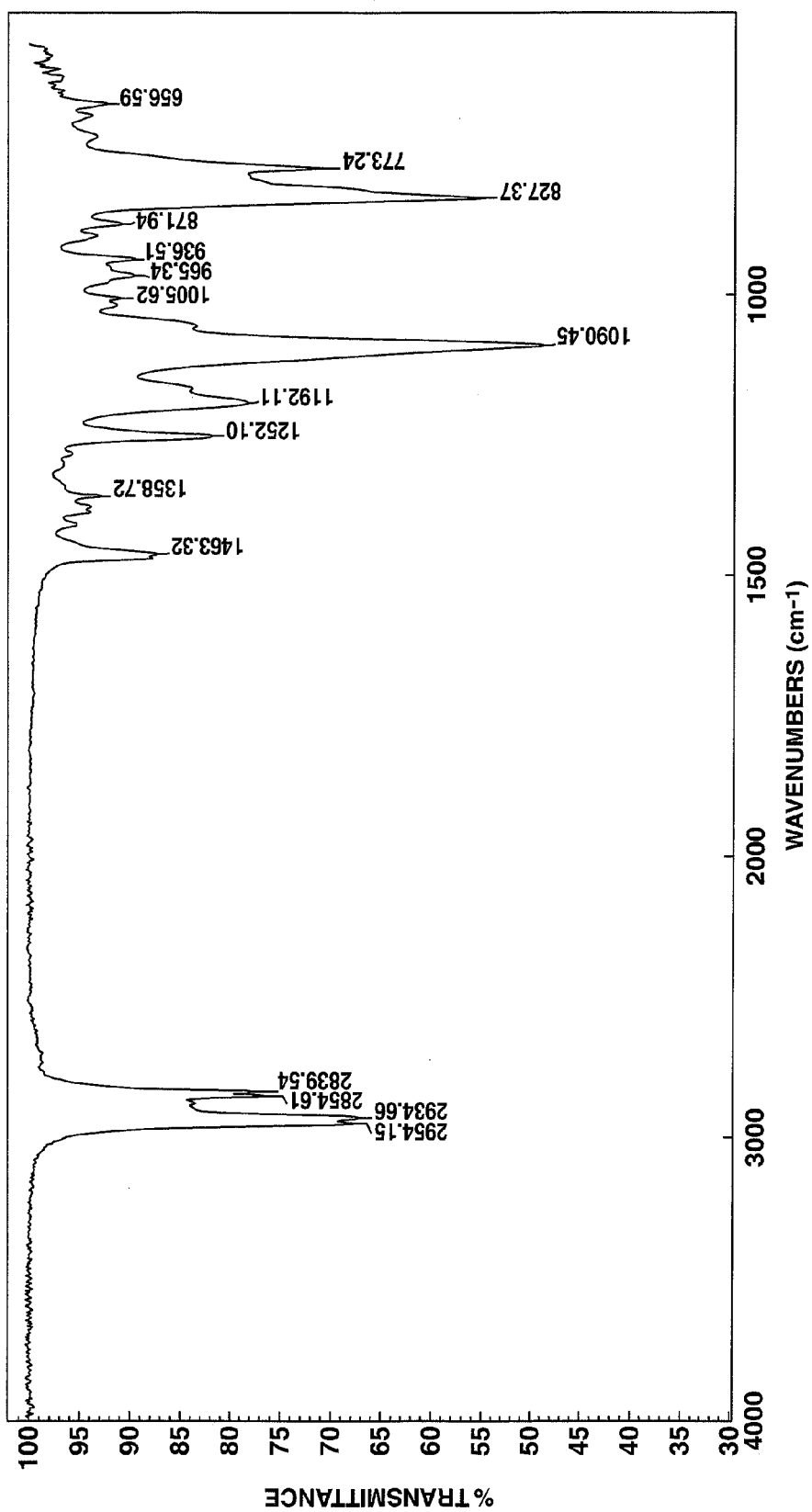

The fraction was analyzed by mass, $^1$H-NMR and IR spectroscopy.
Mass spectrum
m/z 349, 334, 292, 200, 172
$^1$H-NMR spectrum (heavy chloroform solvent)
See the chart of FIG. 1.
IR spectrum
See the chart of FIG. 2.
From these analytical data, the compound was identified to be N-t-butyldimethylsilyl-N-butyl-3-aminopropyltrimethoxysilane.

Example 2

Synthesis of N-t-butyldimethylsilyl-N-butyl-3-aminopropyltrimethoxysilane from N-butyl-3-aminopropyltrimethoxysilane A flask equipped with a stirrer, reflux condenser, dropping funnel and thermometer was charged with 23.5 g (0.1 mol) of N-butyl-3-aminopropyltrimethoxysilane, 11.1 g (0.11 mol) of triethylamine, and 15 ml of toluene and heated at 80° C. Once the internal temperature became steady, 15.0 g of t-butyldimethylchlorosilane in 15 ml of toluene was added dropwise over 1 hour. Stirring was continued at the temperature for a further 12 hours. The resulting salt was removed by filtration. The filtrate was distilled, collecting 29.9 g of a fraction having a boiling point of 128-129° C./0.4 kPa.

The fraction was analyzed by mass, $^1$H-NMR and IR spectroscopy. The spectra were the same as the compound of Example 1. The compound was thus identified to be N-t-butyldimethylsilyl-N-butyl-3-aminopropyltrimethoxysilane.

Example 3

N-t-butyldimethylsilyl-N-butyl-3-aminopropyltriethoxysilane

A flask equipped with a stirrer, reflux condenser, dropping funnel and thermometer was charged with 22.8 g (0.1 mol) of N-t-butyldimethylsilyl-N-butyl-N-allylamine and 0.07 g of a toluene solution of platinum/1,3-divinyl-1,1,3,3-tetramethyldisiloxane complex (Pt concentration 3 wt %) and heated at 50° C. Once the internal temperature became steady, 16.4 g (0.1 mol) of triethoxysilane was added dropwise over 1 hour. Stirring was continued at the temperature for a further 1 hour. The reaction solution was distilled, collecting 31.4 g of a fraction having a boiling point of 144-146° C./0.4 kPa.

The fraction was analyzed by mass, $^1$H-NMR and IR spectroscopy.

Mass spectrum m/z 391, 376, 260, 200, 186

$^1$H-NMR spectrum (heavy chloroform solvent)

Figure 3:
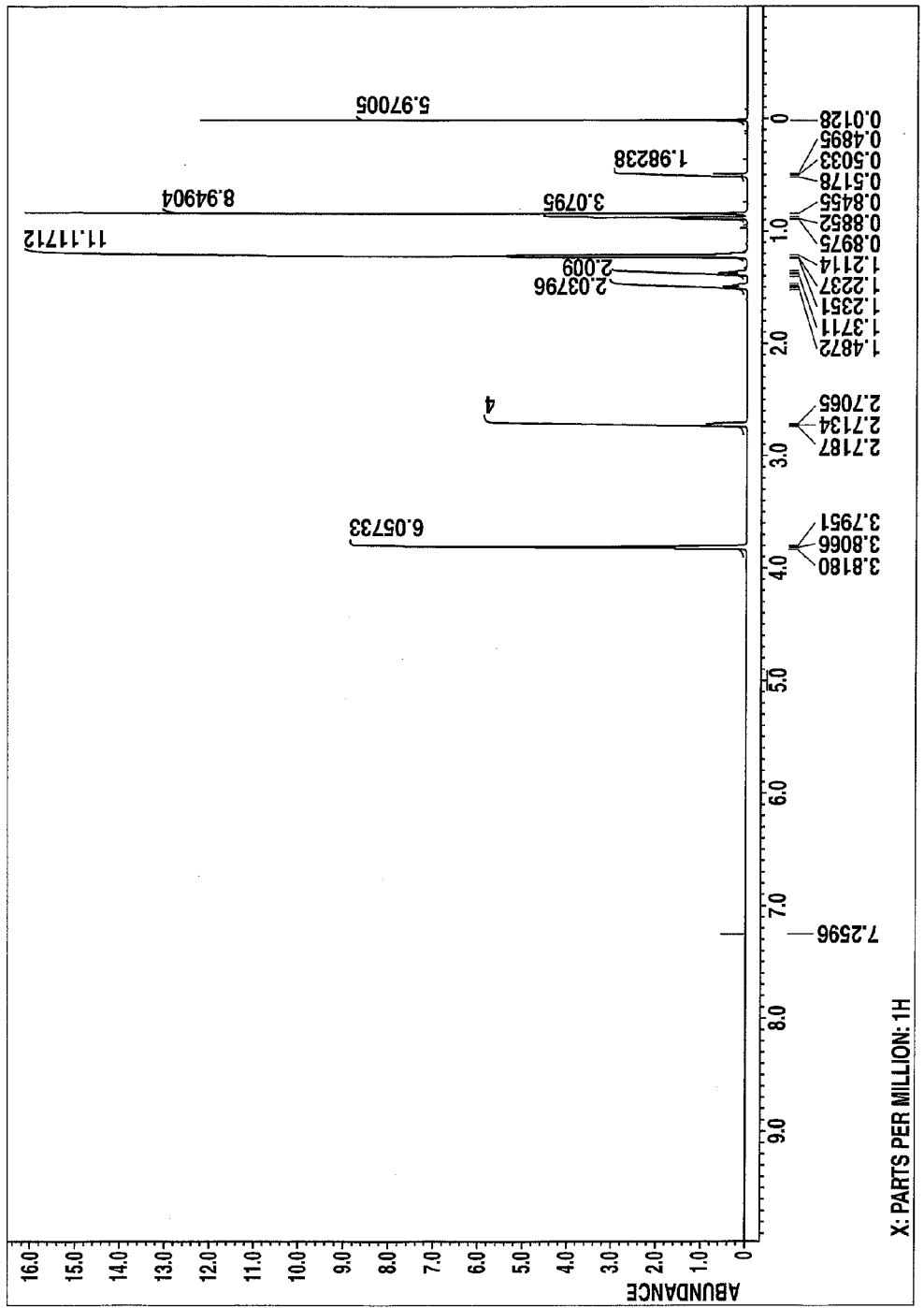
FIGS. 3 and 4 diagrammatically illustrate the $^1$H-NMR and IR spectra of N-t-butyldimethylsilyl-N-butyl-3-aminopropyl-triethoxysilane obtained in Example 3, respectively.

See the chart of FIG. 3.

IR spectrum

Figure 4:
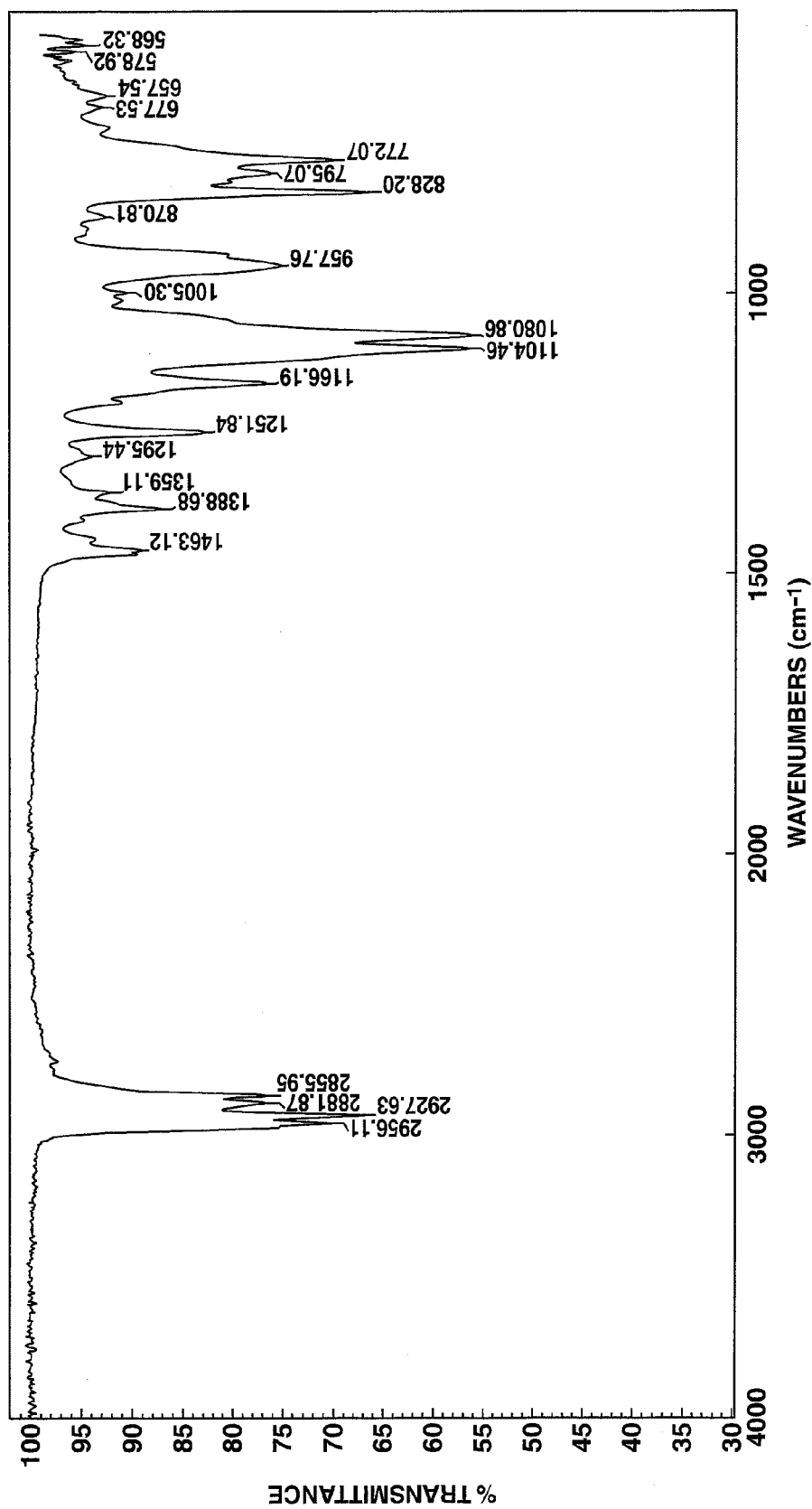

See the chart of FIG. 4.

From these analytical data, the compound was identified to be N-t-butyldimethylsilyl-N-butyl-3-aminopropyltriethoxysilane.

Example 4

N-t-butyldimethylsilyl-N-benzyl-3-aminopropyltrimethoxysilane

A flask equipped with a stirrer, reflux condenser, dropping funnel and thermometer was charged with 26.2 g (0.1 mol) of N-t-butyldimethylsilyl-N-benzyl-N-allylamine and 0.07 g of a toluene solution of platinum/1,3-divinyl-1,1,3,3-tetramethyldisiloxane complex (Pt concentration 3 wt %) and heated at 50° C. Once the internal temperature became steady, 12.2 g (0.1 mol) of trimethoxysilane was added dropwise over 1 hour. Stirring was continued at the temperature for a further 1 hour. The reaction solution was distilled, collecting 32.6 g of a fraction having a boiling point of 165-166° C./0.4 kPa.

The fraction was analyzed by mass, $^1$H-NMR and IR spectroscopy.

Mass spectrum m/z 383, 368, 326, 234, 206, 91

$^1$H-NMR spectrum (heavy chloroform solvent)

Figure 5:
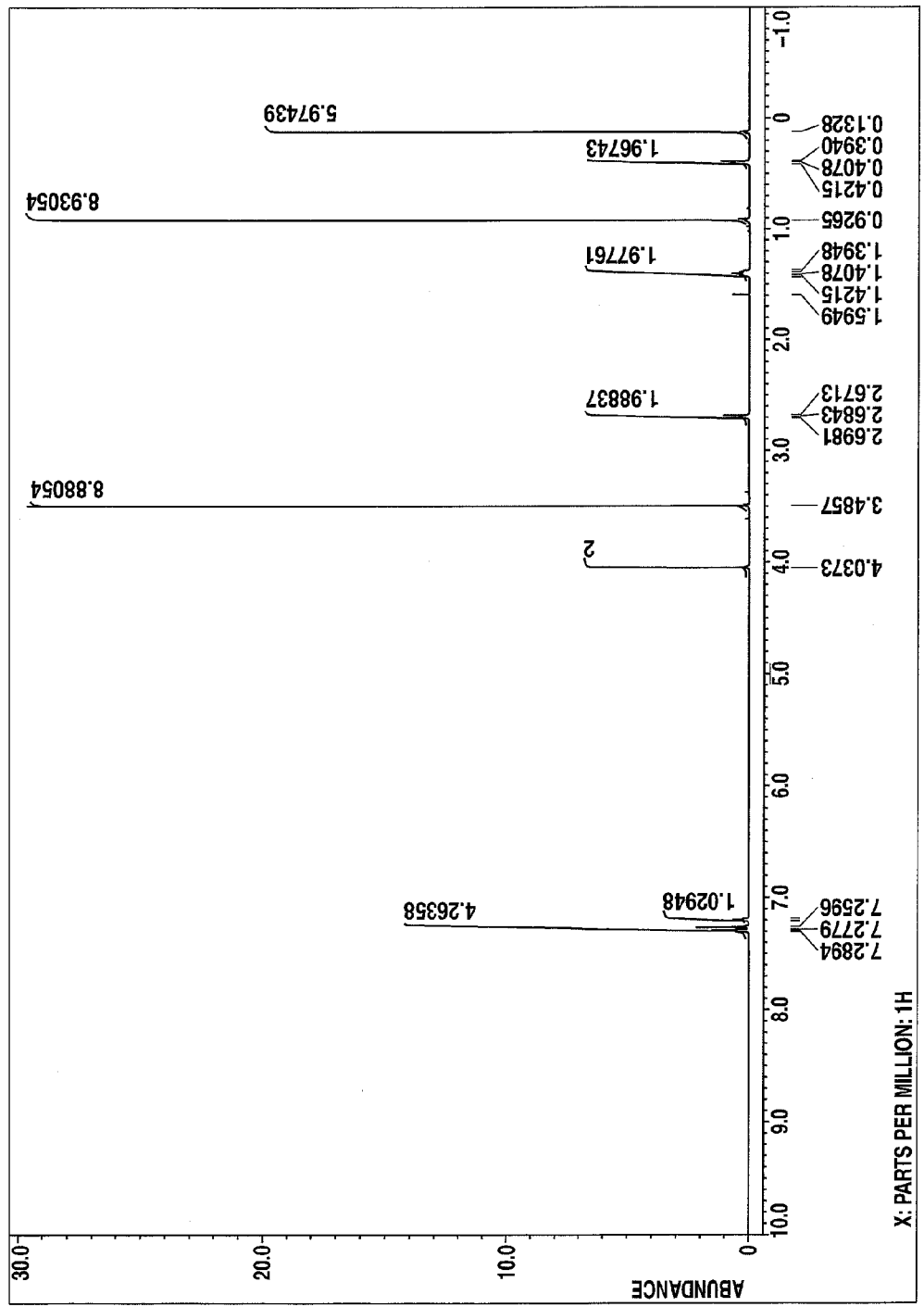
FIGS. 5 and 6 diagrammatically illustrate the $^1$H-NMR and IR spectra of N-t-butyldimethylsilyl-N-benzyl-3-aminopropyl-trimethoxysilane obtained in Example 4, respectively.

See the chart of FIG. 5.

IR spectrum

Figure 6:
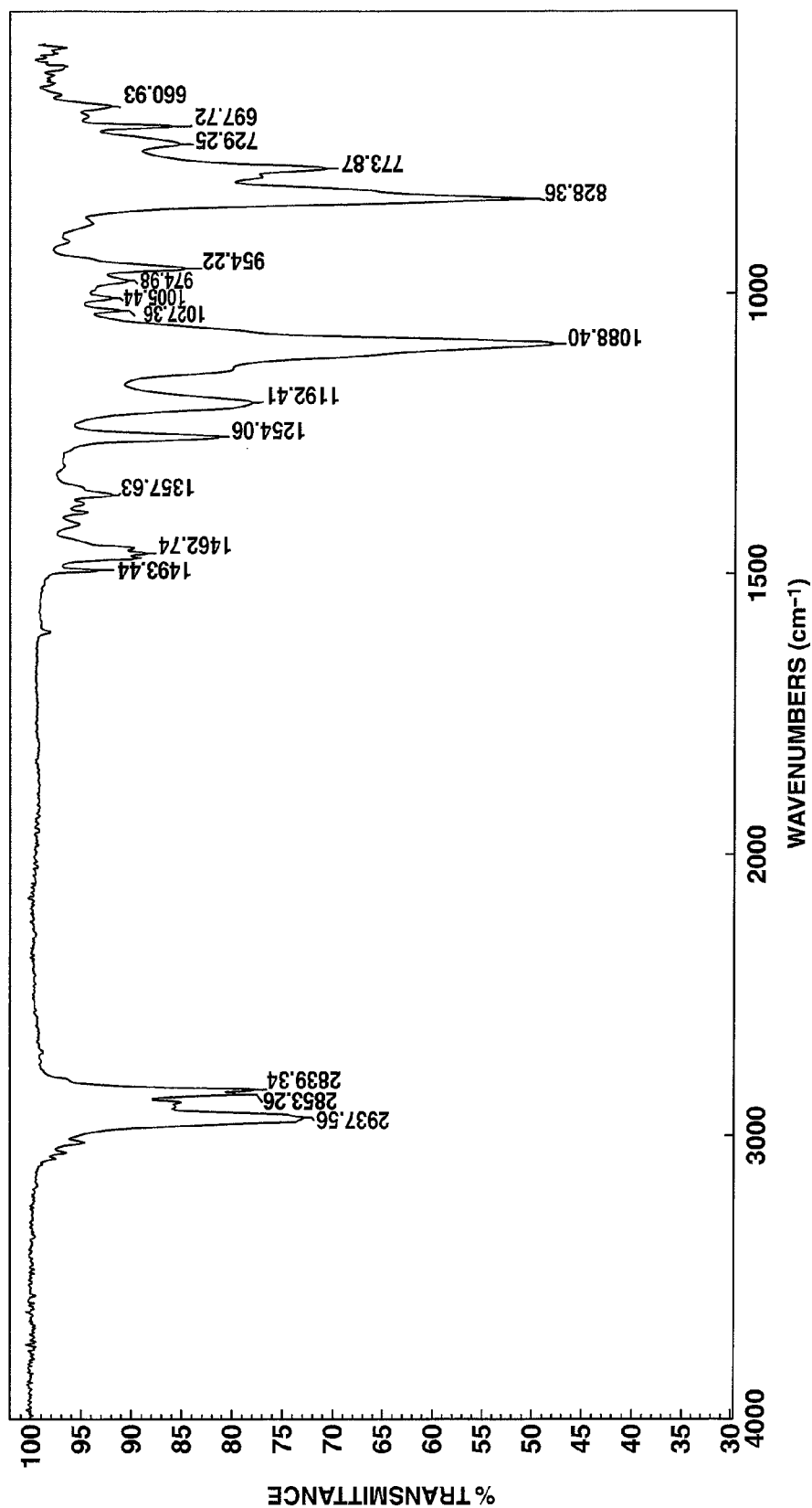

See the chart of FIG. 6.

From these analytical data, the compound was identified to be N-t-butyldimethylsilyl-N-benzyl-3-aminopropyltrimethoxysilane.

Example 5

N-t-butyldimethylsilyl-N-benzyl-3-aminopropylmethyldiethoxysilane

A flask equipped with a stirrer, reflux condenser, dropping funnel and thermometer was charged with 26.2 g (0.1 mol) of N-t-butyldimethylsilyl-N-benzyl-N-allylamine and 0.07 g of a toluene solution of platinum/1,3-divinyl-1,1,3,3-tetramethyldisiloxane complex (Pt concentration 3 wt %) and heated at 50° C. Once the internal temperature became steady, 13.4 g (0.1 mol) of methyldiethoxysilane was added dropwise over 1 hour. Stirring was continued at the temperature for a further 1 hour. The reaction solution was distilled, collecting 31.0 g of a fraction having a boiling point of 169-170° C./0.4 kPa.

The fraction was analyzed by mass, $^1$H-NMR and IR spectroscopy.

Mass spectrum m/z 395, 380, 338, 234, 190, 91

$^1$H-NMR spectrum (heavy chloroform solvent)

Figure 7:
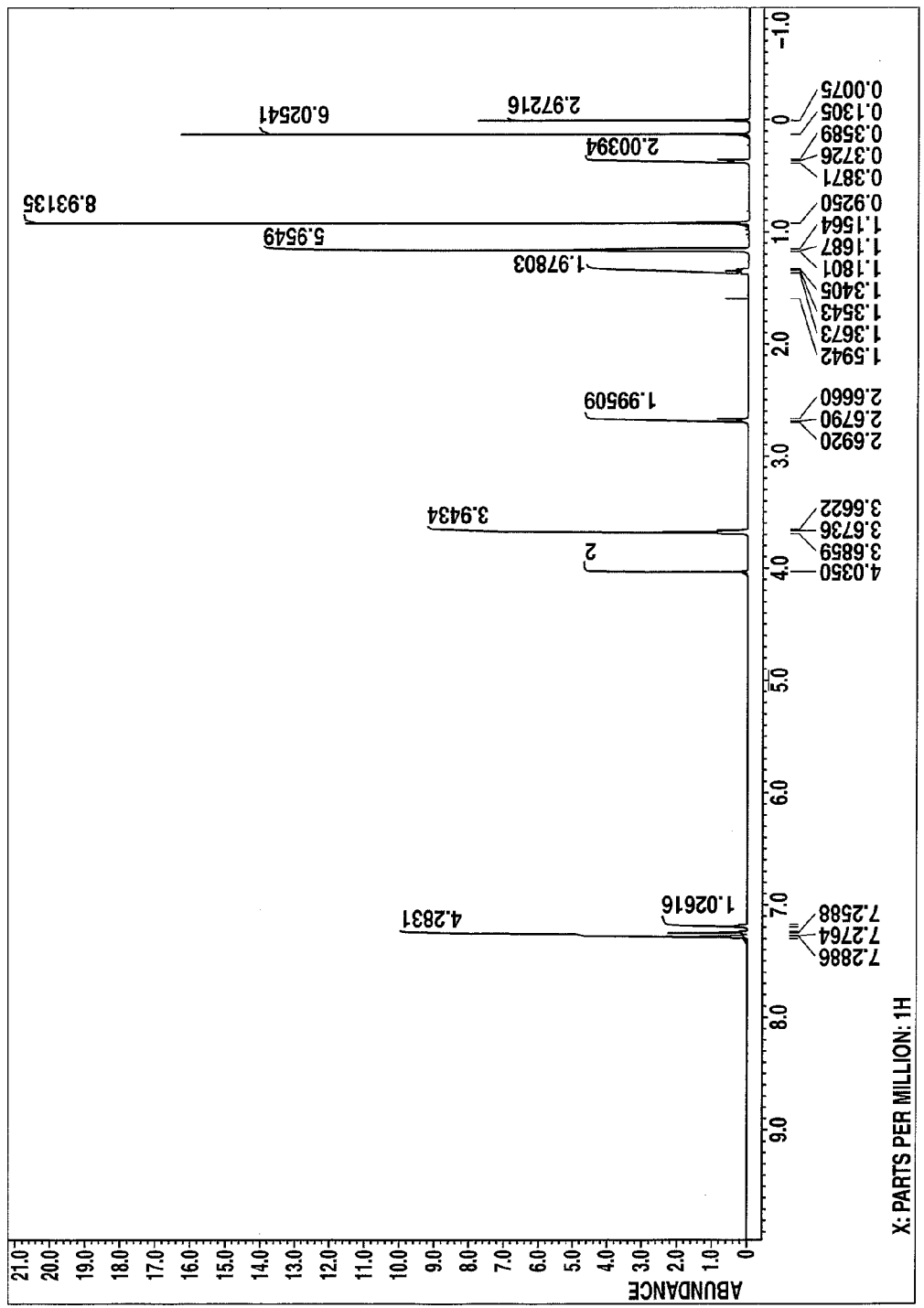
FIGS. 7 and 8 diagrammatically illustrate the $^1$H-NMR and IR spectra of N-t-butyldimethylsilyl-N-benzyl-3-aminopropyl-methyldiethoxysilane obtained in Example 5, respectively.

See the chart of FIG. 7.

IR spectrum

Figure 8:
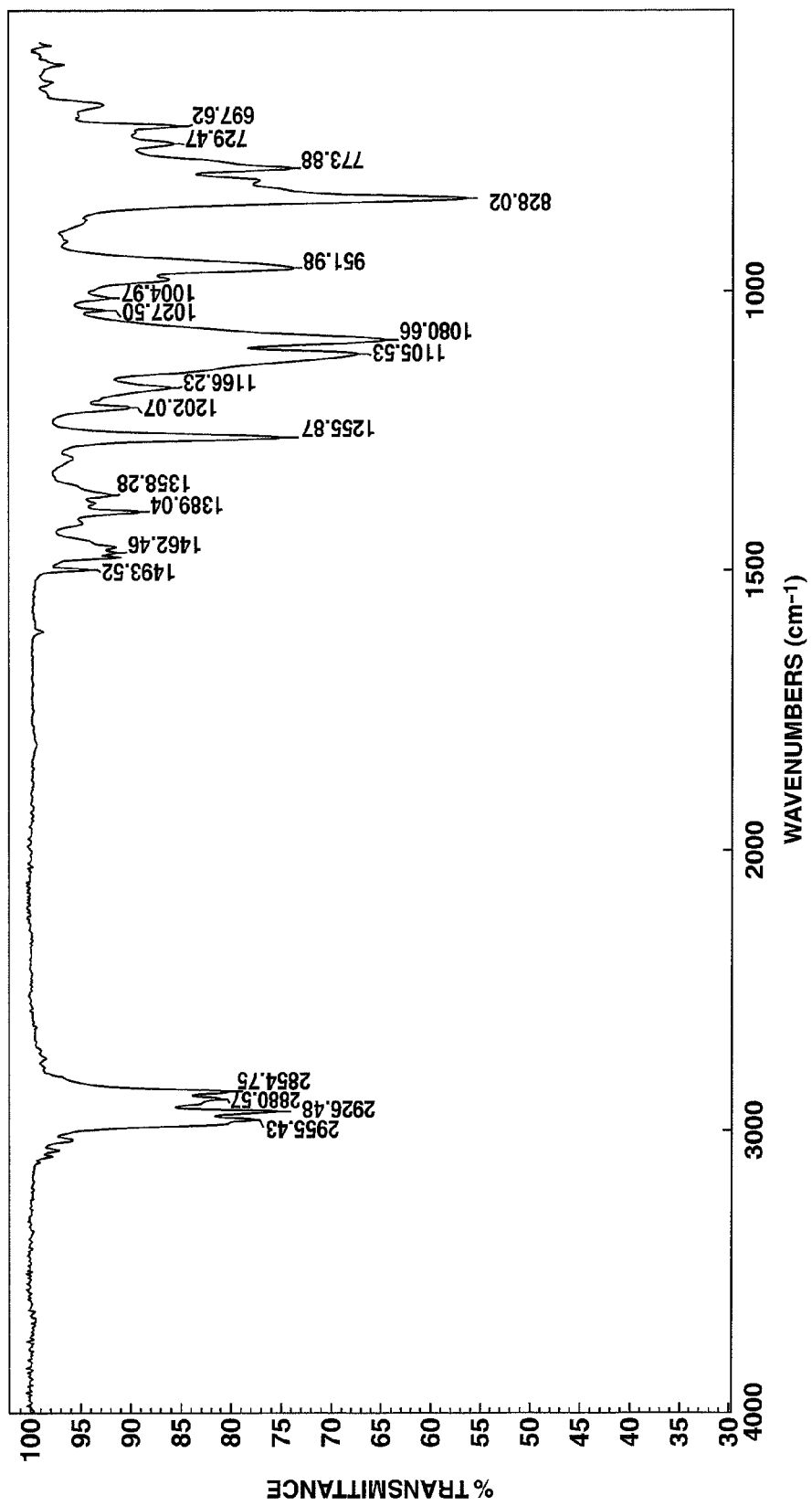

See the chart of FIG. 8.

From these analytical data, the compound was identified to be N-t-butyldimethylsilyl-N-benzyl-3-aminopropylmethyldiethoxysilane.

Example 6

N-triethylsilyl-N-benzyl-3-aminopropyltrimethoxysilane

A flask equipped with a stirrer, reflux condenser, dropping funnel and thermometer was charged with 26.2 g (0.1 mol) of N-triethylsilyl-N-benzyl-N-allylamine and 0.07 g of a toluene solution of platinum/1,3-divinyl-1,1,3,3-tetramethyldisiloxane complex (Pt concentration 3 wt %) and heated at 50° C. Once the internal temperature became steady, 12.2 g (0.1 mol) of trimethoxysilane was added dropwise over 1 hour. Stirring was continued at the temperature for a further 1 hour. The reaction solution was distilled, collecting 32.6 g of a fraction having a boiling point of 144-146° C./0.1 kPa.

The fraction was analyzed by mass, $^1$H-NMR and IR spectroscopy.

Mass spectrum m/z 383, 234, 206, 115, 91, 87

$^1$H-NMR spectrum (heavy chloroform solvent)

Figure 9:
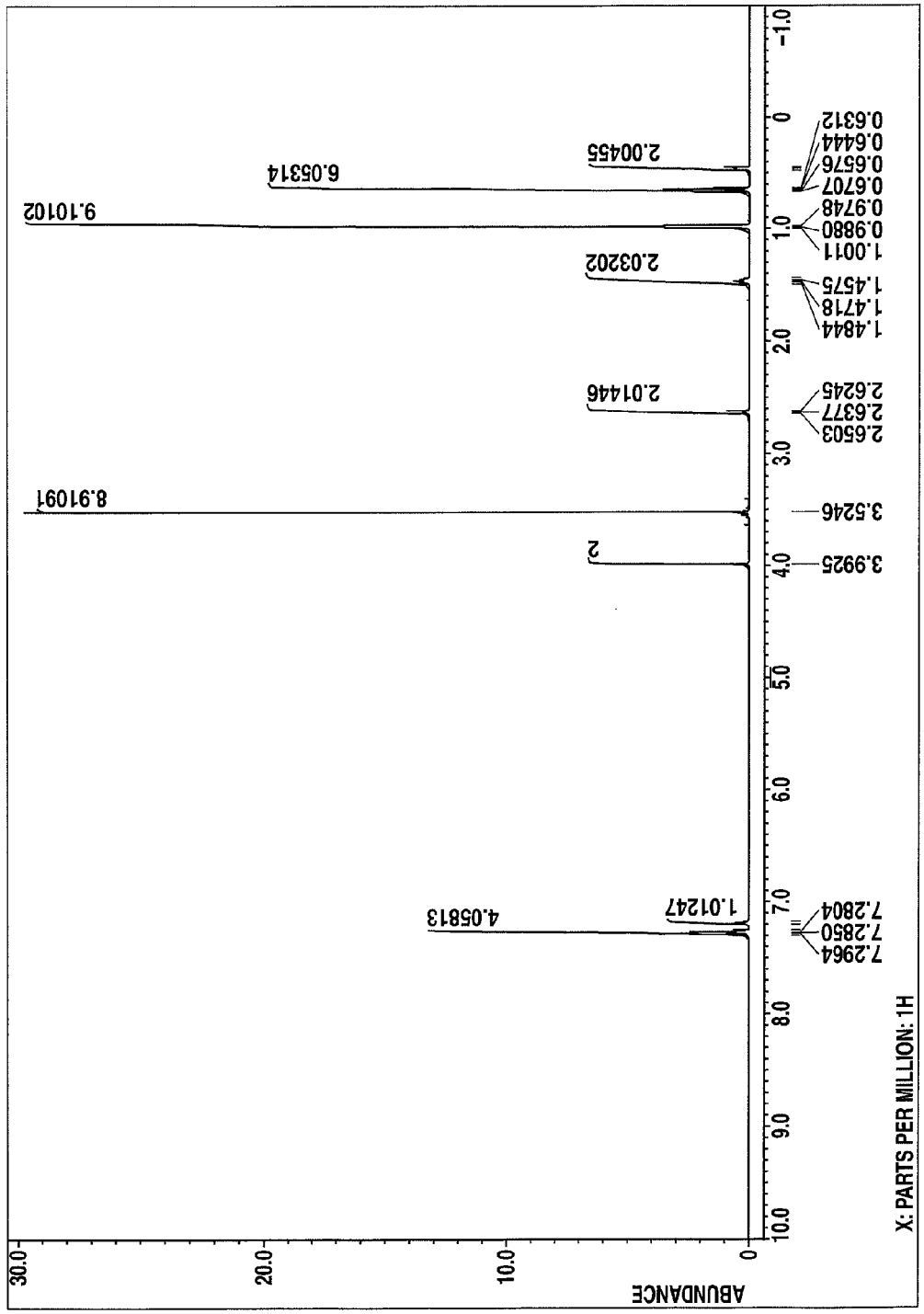
FIGS. 9 and 10 diagrammatically illustrate the $^1$H-NMR and IR spectra of N-triethylsilyl-N-benzyl-3-aminopropyl-trimethoxysilane obtained in Example 6, respectively.

See the chart of FIG. 9.

IR spectrum

Figure 10:
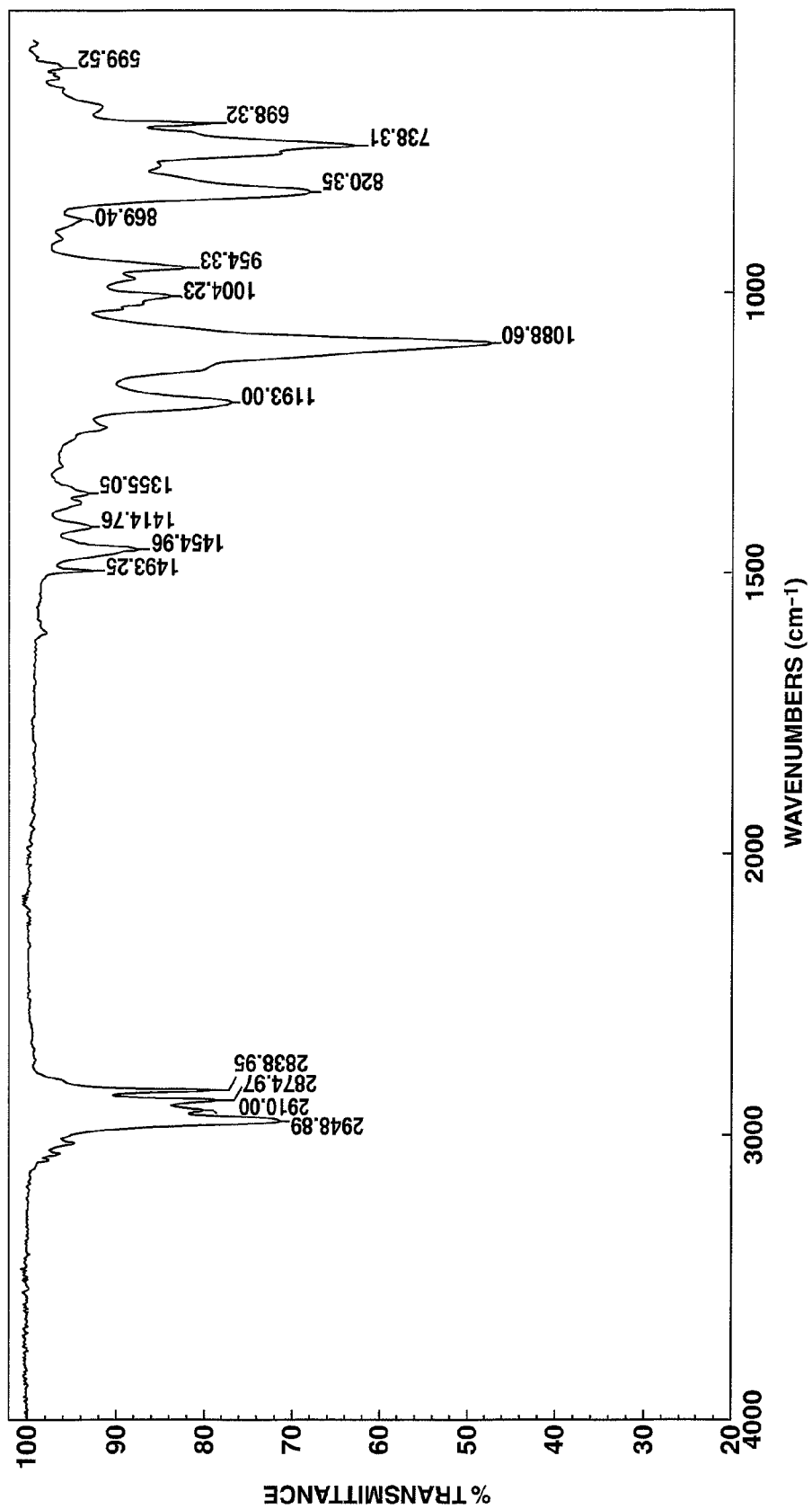

See the chart of FIG. 10.

From these analytical data, the compound was identified to be N-triethylsilyl-N-benzyl-3-aminopropyltrimethoxysilane.

Example 7

N-triethylsilyl-N-benzyl-3-aminopropylmethyldiethoxysilane

A flask equipped with a stirrer, reflux condenser, dropping funnel and thermometer was charged with 26.2 g (0.1 mol) of N-triethylsilyl-N-benzyl-N-allylamine and 0.07 g of a toluene solution of platinum/1,3-divinyl-1,1,3,3-tetramethyldisiloxane complex (Pt concentration 3 wt %) and heated at 50° C. Once the internal temperature became steady, 13.4 g (0.1 mol) of methyldiethoxysilane was added dropwise over 1 hour. Stirring was continued at the temperature for a further 1 hour. The reaction solution was distilled, collecting 31.0 g of a fraction having a boiling point of 151-152° C./0.1 kPa.

The fraction was analyzed by mass, $^1$H-NMR and IR spectroscopy.

Mass spectrum m/z 395, 380, 234, 190, 91, 87

$^1$H-NMR spectrum (heavy chloroform solvent)

Figure 11:
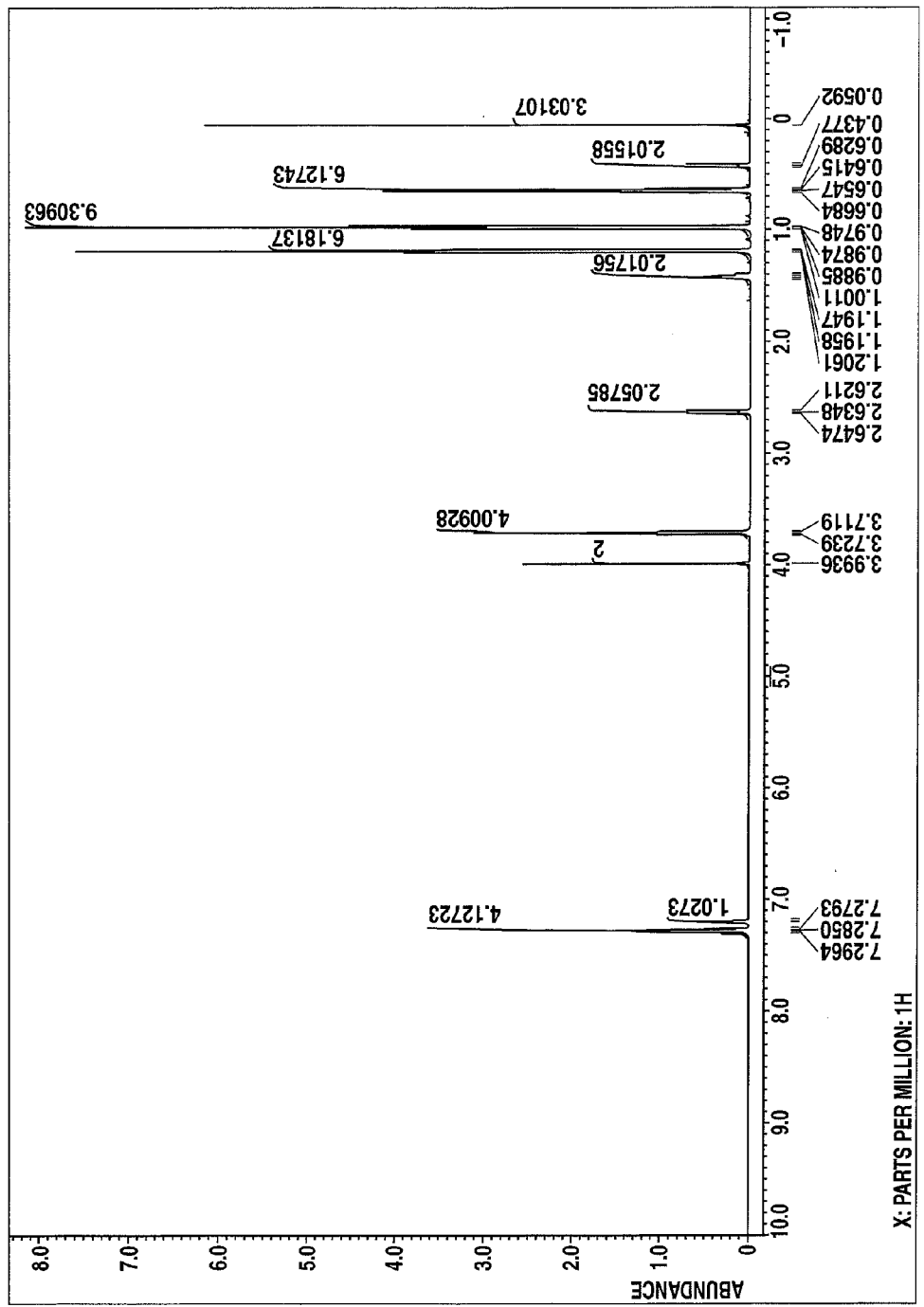
FIGS. 11 and 12 diagrammatically illustrate the $^1$H-NMR and IR spectra of N-triethylsilyl-N-benzyl-3-aminopropyl-methyldiethoxysilane obtained in Example 7, respectively.

See the chart of FIG. 11.

IR spectrum

Figure 12:
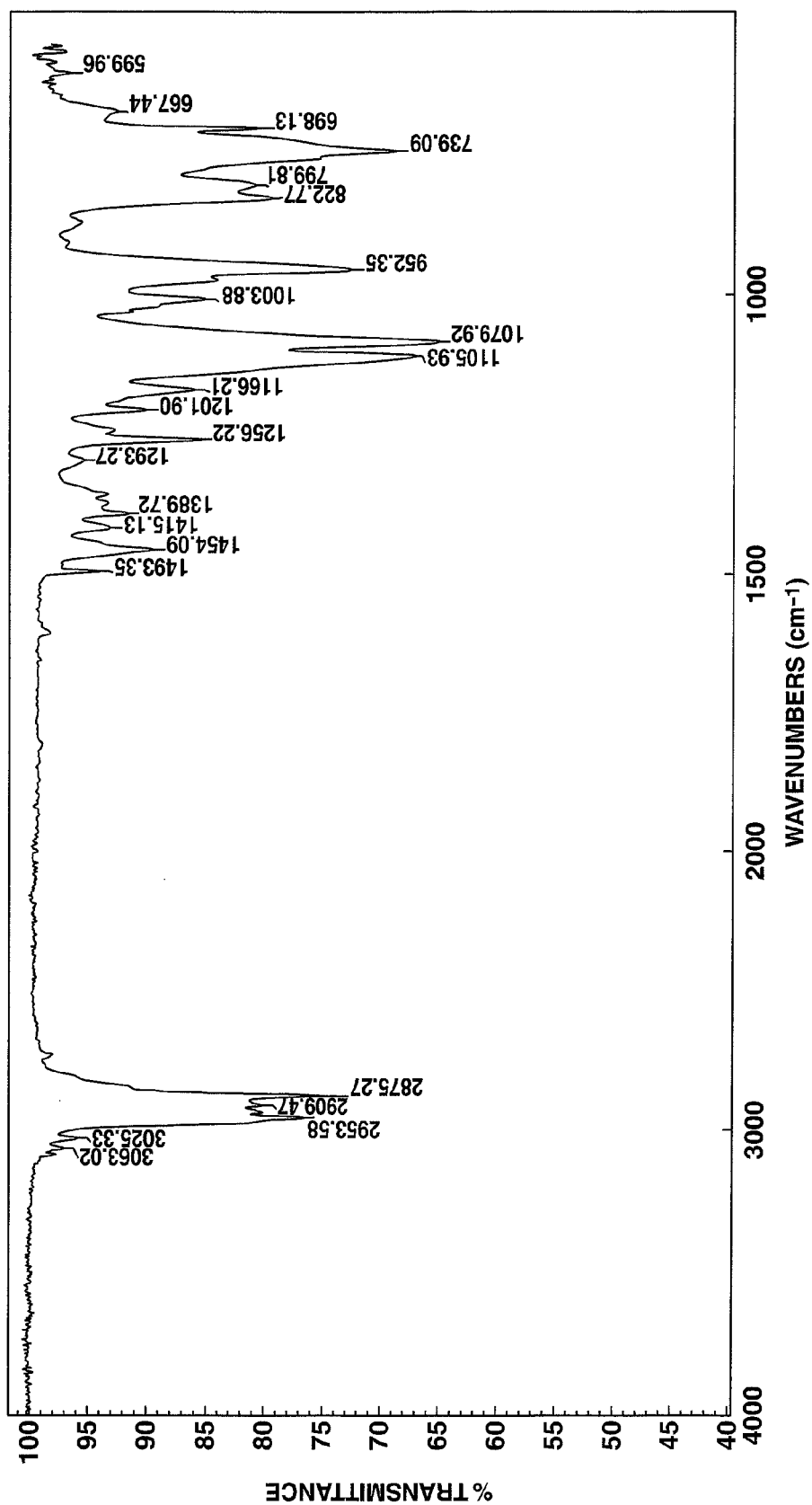

See the chart of FIG. 12.

From these analytical data, the compound was identified to be N-triethylsilyl-N-benzyl-3-aminopropylmethyldiethoxysilane.

Japanese Patent Application No. 2012-1014369 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organoxysilane compound having a silyl-protected secondary amino group, represented by the general formula (1):

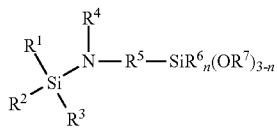
(1)

wherein i) $R^1$ is a substituted or unsubstituted, secondary or tertiary, monovalent hydrocarbon group of 3 to 20 carbon atoms, and $R^2$, $R^3$, $R^4$, $R^6$ and $R^7$ each are a substituted or unsubstituted, monovalent hydrocarbon group of 1 to 20 carbon atoms, or ii) $R^1$, $R^2$ and $R^3$ each are a substituted or unsubstituted, monovalent hydrocarbon group of 2 to 20 carbon atoms, and $R^4$, $R^6$ and $R^7$ each are a substituted or unsubstituted, monovalent hydrocarbon group of 1 to 20 carbon atoms, and in either case, $R^5$ is a straight or branched divalent hydrocarbon group of 1 to 20 carbon atoms, and n is 0 or 1.

2. The organoxysilane compound of claim 1 wherein the $R^1R^2R^3Si-$ group is t-butyldimethylsilyl or triisopropylsilyl.

3. A method of preparing the organoxysilane compound of claim 1, comprising reacting a compound having the general formula (2):

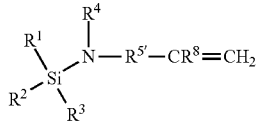
(2)

wherein $R^1$, $R^2$, $R^3$, and $R^4$ are as defined above, $R^8$ is hydrogen or methyl, $R^{5'}$ is a straight or branched divalent hydrocarbon group of 1 to 18 carbon atoms when $R^8$ is hydrogen, or $R^{5'}$ is a straight or branched divalent hydrocarbon group of 1 to 17 carbon atoms when $R^8$ is methyl, with a hydrogensilane compound having the general formula (3):

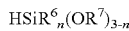
(3)

wherein $R^6$, $R^7$ and n are as defined above, in the presence of a platinum catalyst.

4. A method of preparing the organoxysilane compound of claim 1, comprising silylating a compound having the general formula (4):

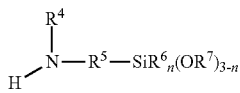
(4)

wherein $R^4$, $R^5$, $R^6$, $R^7$ and n are as defined above, with a silylating agent having a $R^1R^2R^3Si-$ group wherein $R^1$, $R^2$ and $R^3$ are as defined above.

* * * * *